Figure 1:
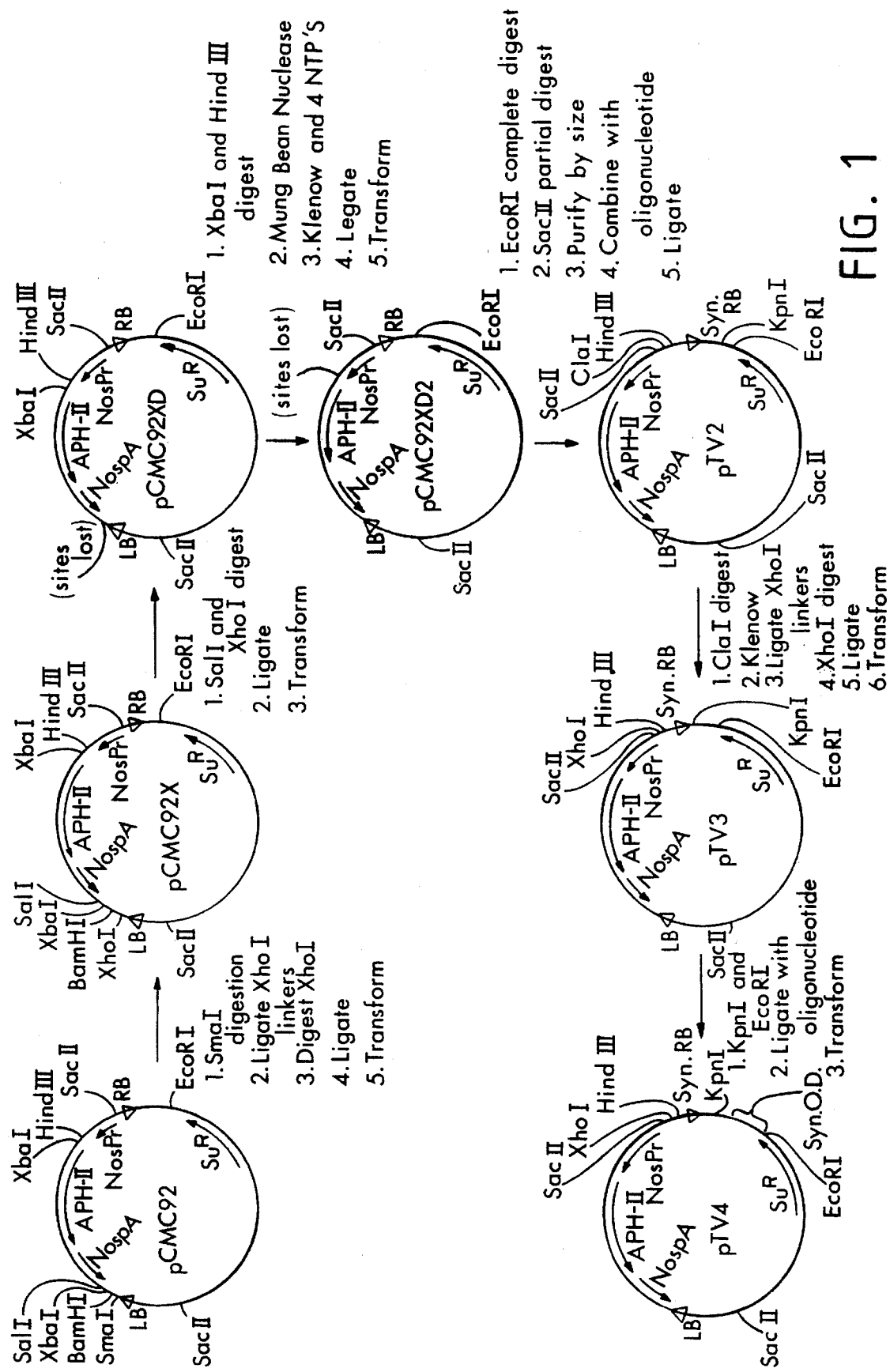

US005608142A

United States Patent [19]
Barton et al.

[11] Patent Number: 5,608,142
[45] Date of Patent: Mar. 4, 1997

[54] INSECTICIDAL COTTON PLANTS

[75] Inventors: Kenneth A. Barton, Middleton; Paul F. Umbeck, Madison, both of Wis.

[73] Assignee: Agracetus, Inc., Middleton, Wis.

[21] Appl. No.: 299,767

[22] Filed: Jan. 23, 1989

Related U.S. Application Data

[63] Continuation-in-part of Ser. No. 123,054, Nov. 19, 1987, abandoned, and a continuation-in-part of Ser. No. 937,384, Dec. 3, 1986, Pat. No. 5,004,863.

[51] Int. Cl.$^6$ ..................................................... A01H 4/00
[52] U.S. Cl. .................. 800/205; 800/255; 800/DIG. 27; 435/320.1
[58] Field of Search ................................... 536/27, 23.71; 435/317.1, 240.4, 320.1; 935/30, 35, 67; 800/205, 255, DIG. 27, DIG. 43

[56] References Cited

U.S. PATENT DOCUMENTS

| | | | |
|---|---|---|---|
| 4,448,885 | 5/1984 | Schnepf et al. | 435/252.33 |
| 4,467,036 | 8/1984 | Schnepf et al. | 435/320.1 |
| 4,820,639 | 4/1989 | Gehrke | 435/172.3 |
| 5,159,135 | 10/1992 | Umbeck | 800/205 |
| 5,254,799 | 10/1993 | De Greve et al. | 800/205 |

FOREIGN PATENT DOCUMENTS

| | | |
|---|---|---|
| 142924 | 5/1985 | European Pat. Off. . |
| 178151 | 4/1986 | European Pat. Off. . |
| 186379 | 7/1986 | European Pat. Off. . |
| 0193259 | 9/1986 | European Pat. Off. ........ C12N 15/00 |
| 193259 | 9/1986 | European Pat. Off. . |
| 200708 | 11/1986 | European Pat. Off. . |
| 2165261 | 4/1986 | United Kingdom . |

OTHER PUBLICATIONS

Gehrke et al. (1983) Biochemistry 22:5157–64.
Schnepf et al (1985) Journ. Biol. Chem. 260 (10):6273–80.
White et al. (1968) Principles of Biochemistry, Fourth Ed., Mc Graw–Hill Book Company, NY, p. 144.
Umbeck et al (Mar. 1987) Bio/Technology 5:263–266.
Hofte et al (Jun. 1989) Microbiological Reviews 53:242–255.
Vasil (Apr. 1988) Bio/Technology 6:397–402.
Schnepf et al (1985) Journal of Biological Chemistry 260:6264–6272.
Barton et al (1987) Plant Physiol. 85:1103–1109.
Vaeek et al (Jul. 1987) Nature 328:33–37.
Fischhoff et al (1987) Bio/Technology 5:807–813.
Knowles et al (1988) Molecular Microbiology 2(1):153–157.
Barton, et al., "Regeneration of Intact Tobacco Plants Containing Full Length Copies of Genetically Engineered T–DNA, and Transmission of T–DNA to Rl Progeny", *Cell*, vol. 32, 1033–1043 (Apr. 1983).
Gehrke, et al., "5'–Conformation of Capped Alfalfa Mosaic Virus Ribonucleic Acid 4 May Reflect Its Independence of the Cap Structure or of Cap–Binding Protein for Efficient Translation," *Biochem.*, vol. 22, pp. 5157–5164 (1983).

Peralta, et al., "Overdrive, a T–DNA Transmission Enhancer on the A. Tumefaciens Tumour–Inducing Plasmid," *EMBO Journal*, vol. 5, No. 6, pp. 1137–1142 (1986).
Saiki, et al., "Enzymatic Amplification of B–Globin Genomic Sequences and Restriction Site Analysis for Diagnosis of Sickle Cell Anemia," *Science*, vol. 230, pp. 1350–1354 (1985).
Schnepf, et al., "The Amino Acid Sequence of a Crystal Protein from *Bacillus thuringiensis* Deduced from the DNA Base Sequence," *J. Biol. Chem.*, vol. 260, pp. 6264–6272 (1985).
Umbeck, et al., "Genetically Transformed Cotton (Gossypium Hirsutum L.) Plants," *Bio/Technology*, vol. 5, No. 3, pp. 263–266 (1987).
Barton, K. A., et al., "*Bacillus thuringiensis* –Endotoxin Expressed in Transgenic Nicotiana tabacum Provides Resistance to Lepidopteran Insects," *Plant Physiol.*, vol. 85, pp. 1103–1109 (1987).
Fischhoff, D. A., et al., "Insect Tolerant Transgenic Tomato Plants," *Bio/Technology*, vol. 5, pp. 807–813 (1987).
Gronenborn, B., et al., "Propagation of Foreign DNA in Plants Using Cauliflower Mosaic Virus As Vector," *Nature*, vol. 294, pp. 773–776 (1981).
Spear, Brian B., "Genetic Engineering of Bacterial Insecticides," Biotechnology In Agricultural Chemistry (Chapter 17), The American Chemical Society, pp. 204–214 (1987).
Vaeck, et al., "Transgenic Plants Protected from Insect Attack," *Nature*, vol. 328, pp. 33–37 (1987).
Aronson, A. I., et al., "*Bacillus thuringiensis* and Related Insect Pathogens," *Microbiol. Rev.*, vol. 50, pp. 1–24 (1986).
Rowe, G. E. and A. Margaritis, "Bioprocess Deveopments in the Production of Bioinsecticides by *Bacillus thuringiensis*," *Crit. Rev. Biotechnol.*, vol. 6 pp. 87–127 (1987).
Sneh, B., et al., "Improvement of the Insecticidal Activity of *Bacillus thuringiensis* var. *entomocidus* on Larvae of *Spodoptera littoralis* (Lepidoptera, Noctuidae) By Addition of Chitinolytic Bacteria, a Phagostimulant and a UV–protectant," *Z. Angew Entomol*, vol. 96, pp. 77–83 (1983).

(List continued on next page.)

*Primary Examiner*—Che S. Chereskin
*Attorney, Agent, or Firm*—Quarles & Brady

[57] ABSTRACT

A plant expression vector is constructed to cause the expression of an amino-terminal portion of the *Bacillus thuringiensis* delta-endotoxin gene in plant cells and the vector is used to create transgenic plants expressing the toxin. A truncated form of the toxin is used, with carboxy-terminal prolines added for stability. A translational enhancer sequence derived from the untranslated leader sequence from the mRNA of the coat protein gene of alfalfa mosaic virus coat protein gene is placed between a promoter and the toxin gene to increase translational efficiency. The transgenic plants produced are toxic to Lepidopteran pests and can transmit that trait to their progeny by normal Mendelian inheritance.

7 Claims, 6 Drawing Sheets

OTHER PUBLICATIONS

Whiteley, H. R. and H. E. Schnepf, "The Molecular Biology of Parasporal Crystal Body Formation in *Bacillus thuringiensis*, "*Ann. Rev. Microbial*, vol. 40, pp. 549–576 (1986).

Amann, E. and J. Brosius, "ATG Vectors for Regulated High–Level Expression of Cloned Genes in *Escherichia coli*, " *Gene*, vol. 40, pp. 183–190 (1985).

Bigelow, C. C. and M. Channon, "Hydrophobicities of Amino Acids and Proteins," *CRC Handbook of Biochem. Mol. Biol.*, Ed. 3, vol. 1, pp. 209–243 (1982).

Blake, M. S., et al., "A Rapid, Sensitive Method for Detection of Alkaline Phosphatase–Conjugated Anti–antibody on Western Blots," *Analytical Biochem.*, vol. 136, pp. 175–179 (1984).

Burnette, W. N., "'Western Blotting': Electrophoretic Transfer of Proteins from Sodium Dodecyl Sulfate–Polyacrylamide Gels to Unmodified Nitrocellulose and Radiographic Detection With Antibody and Radioiodinated Protein A," *Anal. Biochem.*, vol. 112, pp. 195–203 (1981).

Chirgwin, J. M., et al., "Isolation of Biologically Active Ribonucleic Acid from Sources Enriched in Ribonuclease," *Biochem.*, vol. 24, pp. 5294–5299 (1979).

Dellaporta, S. L., et al., "Maize DNA Miniprep.", *Mol. Biol. of Plants: A Lab. Course Manual,* Cold Spring Harbor Lab., Cold Spring Harbor, NY, pp. 36–37 (1985).

Depicker, S. L., et al., "Nopaline Synthase" Transcript Mapping and DNA Sequence *J. Mol. Appl. Genet.*, vol. 1, pp. 561–573 (1982).

Gallie, D. R., et al., "The 5'–Leader Sequence of Tobacco Mosaic Virus RNA Enhances the Expression of Foreign Gene Transcripts In Vitro and In Vivo," *Nuc. Acids Res.*, vol. 15, pp. 3257–3273 (1987).

Gardner, R. D., et al., "The Complete Nucleotide Sequence of an Infectious Clone of Cauliflower Mosaic Virus by M13MP7 Shootgun Sequencing," *Nucl. Acid Res.*, vol. 9, pp. 2871–2888 (1981).

Hood, E. E., et al., "The Hypervirulence of *Agrobacterium tumefaciens* A281 Is Encodes in a Region of pTiBo542 Outside of T–DNA," *J. Bacteriol*, vol. 168, pp. 1291–1301 (1986).

John, M. E., et al., "Identification and Characterization of cDNA Clones Specific for Cholesterol Side–Chain Cleavage Cytochrome P–450," *Proc. Natl. Acad. Sci. USA*, vol. 81, pp. 5628–5632 (1984).

Kozak, M., "Comparison of Initiation of Protein Synthesis in Procaryotes, Eucaryotes, and Organelles," *Microbiol. Rev.*, vol. 47, pp. 1–45 (1983).

Murashige, T. and F. Skoog, "A Revised Medium For Rapid Growth and Bioassays With Tobacco Tissue Cultures," *Physiol. Plant*, vol. 15, pp. 473–497 (1962).

Ow, David, et al., "Functional Regions of the Cauliflower Mosaic Virus 35S. RNA Promoter Determined by Use of the Firefly Luciferase Gene as a Reporter of Promoter Activity," *Proc. Natl. Acad. Sci. USA*, vol. 84, pp. 4870–4874 (1987).

Yadav, N. S., et al., "Short Direct Repeats Flank the T–DNA on a Nopaline Ti Plasmid," *Proc. Natl. Acad. Sci. USA*, vol. 79, pp. 6322–6326 (Oct. 1982).

```
   1 GAATTCGAGC TCGCCCTCGA GGAACATGGT GGAGCACGAC ACTCTCGTCT ACTCCAAGAA
  61 TATCAAAGAT ACAGTCTCAG AAGACCAAAG GGCTATTGAG ACTTTTCAAC AAAGGGTAAT
 121 ATCGGGAAAC CTCCTCGGAT TCCATTGCCC AGCTATCTGT CACTTCATCA AAAGGACAGT
 181 AGAAAAGGAA GGTGGCACCT ACAAATGCCA TCATTGCGAT AAAGGAAAGG CTATCGTTCA
 241 AGATGCCTCT GCCGACAGTG GTCCCAAAGA TGGACCCCCA CCCACGAGGA GCATCGTGGA
 301 AAAAGAAGAC GTTCCAACCA CGTCTTCAAA GCAAGTGGAT TGATGTGATA TCTCCACTGA
 361 CGTAAGGGAT GACGCACAAT CCCACTATCC TTCGCAAGAC CCTTCCTCTA TATAAGGAAG
 421 TTCATTTCAT TTGGAGAGGA CCAAGCTTTT TATTTTAAT TTTCTTTCAA ATACTTCCAC
 481 CATGGATAAC AATCCGAACA TCAATGAATG CATTCCTTAT AATTGTTTAA GTAACCCTGA
 541 AGTAGAAGTA TTAGGTGGAG AAAGAATAGA AACTGGTTAC ACCCCAATCG ATATTTCCTT
 601 GTCGCTAACG CAATTTCTTT TGAGTGAATT TGTTCCCGGT GCTGGATTTG TGTTAGGACT
 661 AGTTGATATA ATATGGGGAA TTTTTGGTCC CTCTCAATGG GACGCATTTC CTGTACAAAT
 721 TGAACAGTTA ATTAACCAAA GAATAGAAGA ATTCGCTAGG AACCAAGCCA TTTCTAGATT
 781 AGAAGGACTA AGCAATCTTT ATCAAATTTA CGCAGAATCT TTTAGAGAGT GGGAAGCAGA
 841 TCCTACTAAT CCAGCATTAA GAGAAGAGAT GCGTATTCAA TTCAATGACA TGAACAGTGC
 901 CCTTACAACC GCTATTCCTC TTTTGGCAGT TCAAAATTAT CAAGTTCCTC TTTTATCAGT
 961 ATATGTTCAA GCTGCAAATT TACATTTATC AGTTTGAGA GATGTTTCAG TGTTTGGACA
1021 AAGGTGGGGA TTTGATGCCG CGACTATCAA TAGTCGTTAT AATGATTTAA CTAGGCTTAT
1081 TGGCAACTAT ACAGATTATG CTGTGCGCTG GTACAATACG GGATTAGAGC GTGTATGGGG
1141 ACCGGATTCT AGAGATTGGG TAAGGTATAA TCAATTTAGA AGAGAGCTAA CACTTACTGT
1201 ATTAGATATC GTTGCTCTAT TCTCAAATTA TGATAGTCGA AGGTATCCAA TTCGAACAGT
1261 TTCCCAATTA ACAAGAGAAA TTTATACGAA CCCAGTATTA GAAAATTTTG ATGGTAGTTT
1321 TCGTGGAATG GCTCAGAGAA TAGAACAGAA TATTAGGCAA CCACATCTTA TGGATATCCT
1381 TAATAGTATA ACCATTTATA CTGATGTGCA TAGAGGCTTT AATTATTGGT CAGGGCATCA
1441 AATAACAGCT TCTCCTGTAG GGTTTTCAGG ACCAGAATTC GCATTCCCTT TATTTGGGAA
1501 TGCGGGGAAT GCAGCTCCAC CCGTACTTGT CTCATTAACT GGTTTGGGGA TTTTTAGAAC
1561 ATTATCTTCA CCTTTATATA GAAGAATTAT ACTTGGTTCA GGCCCAAATA ATCAGGAACT
1621 GTTTGTCCTT GATGGAACGG AGTTTTCTTT TGCCTCCCTA ACGACCAACT TGCCTTCCAC
1681 TATATATAGA CAAAGGGGTA CAGTCGATTC ACTAGATGTA ATACCGCCAC AGGATAATAG
1741 TGTACCACCT CGTGCGGGAT TTAGCCATCG ATTGAGTCAT GTTACAATGC TGAGCCAAGC
1801 AGCTGGAGCA GTTTACACCT TGAGAGCTCC AACGTTTTCT TGGCAGCATC GCAGTGCTGA
1861 ATTTAATAAT ATAATTCCTT CATCACAAAT TACACAAATA CCTTTAACAA AATCTACTAA
1921 TCTTGGCTCT GGAACTTCTG TCGTTAAAGG ACCAGGATTT ACAGGAGGAG ATATTCTTCG
1981 AAGAACTTCA CCTGGCCAGA TTTCAACCTT AAGAGTAAAT ATTACTGCAC CATTATCACA
2041 AAGATATCGG GTAAGAATTC GCTACGCTTC TACTACAAAT TTACAATTCC ATACATCAAT
2101 TGACGGAAGA CCTATTAATC AGGGTAATTT TTCAGCAACT ATGAGTAGTG GGAGTAATTT
2161 ACAGTCCGGA AGCTTTAGGA CTGTAGGTTT TACTACTCCG TTTAACTTTT CAAATGGATC
2221 AAGTGTATTT ACGTTAAGTG CTCATGTCTT CAATTCAGGC AATGAAGTTT ATATAGATCG
2281 AATTGAATTT GTTCCGGCAG AAGTAACCTT TGAGGCAGAA TATGATTTAG AAAGAGCACA
2341 AAAGGCGGTG AATGAGCTGT TTACTTCTTC CAATCAAATC GGGTTAAAAA CAGATGTGAC
2401 GGATTATCAT ATTGATCAAC CACCTTAATA GCTGCAGCAA TGGCAACAAC GTTGCCCGGA
2461 TCCCCGGGGA TCGTTCAAAC ATTTGGCAAT AAAGTTTCTT AAGATTGAAT CCTGTTGCCG
2521 GTCTTGCGAT GATTATCATA TAATTTCTGT TGAATTACGT TAAGCATGTA ATAATTAACA
2581 TGTAATGCAT GACGTTATTT ATGAGATGGG TTTTTATGAT TAGAGTCCCG CAATTATACA
2641 TTTAATACGC GATAGAAAAC AAAATATAGC GCGCAAACTA GGATAAATTA TCGCGCGCGG
2701 TGTCATCTAT GTTACTAGAT CCGTCGACCT GCGTTGCTGG CGTTTTTCCA TAGGCTCCGC
2761 CCCCCTGACG AGCATCACAA AAATCGACGC TCAAGTCAGA GGTGGCGAAA CCCGACAGGA
2821 CTATAAAGAT ACCAGGCGTT TCCCCCTGGA AGCTCCCTCG TGCGCTCTCC TGTTCCGACC
2881 CTGCCGCTTA CCGGATACCT GTCCGCCTTT CTCCCTTCGG GAAGCGTGGC GCTTTCTCAA
2941 TGCTCACGCT GTAGGTATCT CAGTTCGGTG TAGGTCGTTC GCTCCAAGCT GGGCTGTGTG
3001 CACGAACCCC CCGTTCAGCC CGACCGCTGC GCCTTATCCG GTAACTATCG TCTTGAGTCC
3061 AACCCGGTAA GACACGACTT ATCGCCACTG GCAGCAGCCA CTGGTAACAG GATTAGCAGA
```

FIG. 4A

```
3121 GCGAGGTATG TAGGCGGTGC TACAGAGTTC TTGAAGTGGT GGCCTAACTA CGGCTACACT
3181 AGAAGGACAG TATTTGGTAT CTGCGCTCTG CTGAAGCCAG TTACCTTCGG AAAAAGAGTT
3241 GGTAGCTCTT GATCCGGCAA ACAAACCACC GCTGGTAGCG GTGGTTTTTT TGTTTGCAAG
3301 CAGCAGATTA CGCGCAGAAA AAAAGGATCT CAAGAAGATC CTTTGATCTT TTCTACGGGG
3361 TCTGACGCTC AGTGGAACGA AAACTCACGT TAAGGGATTT TGGTCATGAG ATTATCAAAA
3421 AGGATCTTCA CCTAGATCCT TTTAAATTAA AAATGAAGTT TTAAATCAAT CTAAAGTATA
3481 TATGAGTAAA CTTGGTCTGA CAGTTACCAA TGCTTAATCA GTGAGGCACC TATCTCAGCG
3541 ATCTGTCTAT TTCGTTCATC CATAGTTGCC TGACTCCCCG TCGTGTAGAT AACTACGATA
3601 CGGGAGGGCT TACCATCTGG CCCCAGTGCT GCAATGATAC CGCGAGACCC ACGCTCACCG
3661 GCTCCAGATT TATCAGCAAT AAACCAGCCA GCCGGAAGGG CCGAGCGCAG AAGTGGTCCT
3721 GCAACTTTAT CCGCCTCCAT CCAGTCTATT AATTGTTGCC GGGAAGCTAG AGTAAGTAGT
3781 TCGCCAGTTA ATAGTTTGCG CAACGTTGTT GCCATTGCTA CAGGCATCGT GGTGTCACGC
3841 TCGTCGTTTG GTATGGCTTC ATTCAGCTCC GGTTCCCAAC GATCAAGGCG AGTTACATGA
3901 TCCCCCATGT TGTGCAAAAA AGCGGTTAGC TCCTTCGGTC CTCCGATCGT TGTCAGAAGT
3961 AAGTTGGCCG CAGTGTTATC ACTCATGGTT ATGGCAGCAC TGCATAATTC TCTTACTGTC
4021 ATGCCATCCG TAAGATGCTT TTCTGTGACT GGTGAGTACT CAACCAAGTC ATTCTGAGAA
4081 TAGTGTATGC GGCGACCGAG TTGCTCTTGC CCGGCGTCAA CACGGGATAA TACCGCGCCA
4141 CATAGCAGAA CTTTAAAAGT GCTCATCATT GGAAAACGTT CTTCGGGGCG AAAACTCTCA
4201 AGGATCTTAC CGCTGTTGAG ATCCAGTTCG ATGTAACCCA CTCGTGCACC CAACTGATCT
4261 TCAGCATCTT TTACTTTCAC CAGCGTTTCT GGGTGAGCAA AAACAGGAAG GCAAAATGCC
4321 GCAAAAAAGG GAATAAGGGC GACACGGAAA TGTTGAATAC TCATACTCTT CCTTTTTCAA
4381 TATTATTGAA GCATTTATCA GGGTTATTGT CTCATGAGCG GATACATATT TGAATGTATT
4441 TAGAAAAATA AACAAATAGG GGTTCCGCGC ACATTTCCCC GAAAAGTGCC ACCTGACGTC
4501 TAAGAAACCA TTATTATCAT GACATTAACC TATAAAAATA GGCGTATCAC GAGGCCCTTT
4561 CGTCTTCAAG AATTAATTCC GCG
```

FIG. 4B

```
  1  MDNNPNINEC IPYNCLSNPE VEVLGGERIE TGYTPIDISL SLTQFLLSEF
 51  VPGAGFVLGL VDIIWGIFGP SQWDAFPVQI EQLINQRIEE FARNQAISRL
101  EGLSNLYQIY AESFREWEAD PTNPALREEM RIQFNDMNSA LTTAIPLLAV
151  QNYQVPLLSV YVQAANLHLS VLRDVSVFGQ RWGFDAATIN SRYNDLTRLI
201  GNYTDYAVRW YNTGLERVWG PDSRDWVRYN QFRRELTLTV LDIVALFSNY
251  DSRRYPIRTV SQLTREIYTN PVLENFDGSF RGMAQRIEQN IRQPHLMDIL
301  NSITIYTDVH RGFNYWSGHQ ITASPVGFSG PEFAFPLFGN AGNAAPPVLV
351  SLTGLGIFRT LSSPLYRRII LGSGPNNQEL FVLDGTEFSF ASLTTNLPST
401  IYRQRGTVDS LDVIPPQDNS VPPRAGFSHR LSHVTMLSQA AGAVYTLRAP
451  TFSWQHRSAE FNNIIPSSQI TQIPLTKSTN LGSGTSVVKG PGFTGGDILR
501  RTSPGQISTL RVNITAPLSQ RYRVRIRYAS TTNLQFHTSI DGRPINQGNF
551  SATMSSGSNL QSGSFRTVGF TTPFNFSNGS SVFTLSAHVF NSGNEVYIDR
601  IEFVPAEVTF EAEYDLERAQ KAVNELFTSS NQIGLKTDVT DYHIDQPP**
```

FIG 5

INSECTICIDAL COTTON PLANTS

CROSS-REFERENCE TO RELATED APPLICATION

This application is a continuation-in-part of application Ser. No. 123,054 filed Nov. 19, 1987, now abandoned, and a continuation-in-part of Ser. No. 937,384 filed Dec. 3, 1986, now U.S. Pat. No. 5,004,863.

FIELD OF THE INVENTION

The present invention relates to the modification by genetic manipulation of plants and plant lines. Specifically, the present invention is directed to the creation of transgenic plants which efficiently produce effective quantities of exogenous proteins in their cells. This engineered protein production may be useful for several purposes, among which is the production of naturally selective pest control protein agents which have the effect of imbuing the plants with inherent resistance to insect predation.

BACKGROUND OF THE INVENTION

It has now been demonstrated that tissues of many plant species may be transformed by exogenous, typically chimeric, genes which are effective to stably transform cells of the tissues. For several species, tissues transformed in this fashion may be regenerated to give rise to whole transgenic or genetically engineered plants. The engineered traits introduced into the transgenic plants by these techniques have proven to be stable and have also proven to be transmissible through normal Mendellian inheritance to the progeny of the regenerated plants. In those species in which the ability to construct transgenic plants has been established and replicated, such as in tobacco, much research focus is logically directed next toward the introduction of useful traits into those plants. One such desirable trait is the production in the plant cells of desired gene products in vivo in the cells of the transgenic plants.

The most common, though by no means unique, method of transformation of plant cells used to date is based on a unique property of the plant pathogen *Agrobacterium tumefaciens*. Natural or wild-type *A. tumefaciens*, in its normal pathogenic process, transmits a portion of a Ti (for Tumor-inducing) plasmid that it harbors to be introduced into the genome of the infected plant host. This portion of the Ti plasmid is referred to as the T-DNA. The Agrobacterium performs this pathogenic transformation in nature to direct the host cells of the plant to become tumorous and to produce a class of plant metabolites called opines on which the Agrobacterium has the unique ability to feed. By removing the genes responsible for tumor induction and opine production from the Ti plasmid, and by substituting for them exogenous chimeric genes of interest, the plant genetic engineer may then use the natural pathogenic process of the *A. tumefaciens* to introduce foreign genes into plant tissues. Because this transformation will generally occur only on somatic plant tissues which have been wounded, its use to date has focused on those species, such as tobacco, which can be regenerated either from individual somatic cells or from embryogenic somatic cell cultures. This technique has proved effective for plant transformations in cotton, tomato, carrot, and petunia, as well as some other species.

Other plant cell transformation techniques are directed toward the direct insertion of DNA into the cytoplasm of plant cells from which it is taken up, by an uncharacterized mechanism, into the genome of the plant. One such technique is electroporation, in which electric shock causes disruption of the cellular membranes of individual plant cells. Plant protoplasts in aqueous solution when subject to electroporation will uptake DNA from the surrounding medium. Another technique involves the physical acceleration of DNA, coated onto small inert particles, either into regenerable plant tissues or into plant germline cells. These techniques widen the range of plant species which may be genetically engineered since they allow for the transformation of a wider variety of tissue types such as embryonic tissues, or germline cells.

Having the ability to introduce foreign DNA constructs into the genome of plants, however, does not in and of itself create useful traits in the modified plants or plant lines. The ability to code for the production of proteins in plant cells can only contribute to making a more useful plant or plant line if the protein offers some advantage in the field to the plant and is produced in the plant cells in quantities effective to accomplish the desired objective. One objective in the creation of transgenic plants is to make plants which are less attractive to potential plant predators or pathogens. A candidate strategy to make plants resistant to certain insect predators is based on a unique protein made by the *Bacillus thuringiensis*, known as the delta-endotoxin or crystal protein. While the various *B. thuringiensis* species have relatively large variations in the DNA coding sequences for their delta-endotoxin proteins, the proteins themselves have a relatively high degree of homology. This toxin is a relatively large protein that has a specific toxicity to Lepidopteran, Dipteran, or Coleopteran insects. While insecticidal peptides made by the *Bacillus thuringiensis* (*B.t.*) species have been approved for use, and have been used, in agriculture for many years, the relatively high cost of producing the protein in quantity and the need for repeated applications of the protein, because of its degradation in the environment, have proved to be limits on the extensive use of these materials. The creation of transgenic plants which generate this biological insecticide by themselves offers a practical mechanism to control susceptible insects without the need for repeated application of other control agents.

A primary target species for the introduction of an effective *B.t.* toxin capability is the crop plant cotton (*Gossypium hirsutum L.*) In the United States, cotton is an agricultural crop with an exceptionally high pesticide requirement, and that requirement often includes formulations of Bt. toxin produced by bacteria. The Lepidopteran pests of cotton include the tobacco budworm (*Heliothis virescens*), the corn earworm (*Heliothis zea*), also called the cotton bollworm, and the beet armyworm (*Spodoptera frugiperda*). Because of the long regeneration time required to regenerate whole cotton plants from transformed tissues, however, it is practical to use tobacco as a model species to demonstrate and test vector and gene constructions and expression strategies. The inventors here have previously demonstrated the ability to adapt transformation and expression techniques from tobacco to the successful transformation and regeneration of cotton plants and lines. Umbeck et al., "Genetically Transformed Cotton (*Gossypium hirsutum L.*) Plants," *Bio/Technology*, 5, pp 263–266 (1987).

Another consideration in the genetic transformation of plants to express useful proteins is the method of construction of appropriate chimeric DNA sequences which are practically effective to achieve practical transcription and translation levels of the foreign gene products in plant cells. To be effective, a foreign DNA sequence containing a coding region must be flanked by appropriate promotion and control regions. Commonly used plant cell transcription promoters include the nopaline synthase promoter from the T-DNA of *A. tumefaciens* and the 35S promoter from the cauliflower mosaic virus. These promoters are effective in most plant cells but the level of transcription and translation activities of protein coding sequences placed down stream of these promoters is quite variable, depending on several factors such as insertion site or sites and copy number of insertions. Other variables, such as untranslated portions of the transcription product and the polyadenylation sequence also effect the level of translational activity of the coded gene product.

Specifically with regard to the crystal protein of *Bacillus thuringiensis*, it has been previously demonstrated that the crystal protein itself consists of one or more species of a large protein up to 160 kilodaltons in size. This large protein is now referred to as a protoxin, since it has been determined that the protoxin may be cleaved by proteolysis (and is so cleaved in the insect gut) to produce an active peptide toxin of a molecular weight of 55 to 75 kilodaltons that retains the specific toxicity to the target insects. Deletion analysis has localized the toxic portion of the protoxin to the amino terminal end of the protoxin and have demonstrated that both amino- and carboxy-terminal fusions can be made to the toxin without loss of insecticidal activity. The function of the remaining carboxyl portions of the protoxin, beyond structural considerations in crystal protein formation, remains unknown.

While expression of several model proteins in model plant species has proved a regularly replicable process, some proteins present special problems. The *B.t.* protoxin molecule is very large and quite insoluble. The expression of this protein in regenerated transgenic plants has proven to be difficult. The coding sequence for the protein can reliably be inserted into normally competent plant transformation and expression vectors, but the recovery and regeneration of expressing tissues is difficult. Tissues in culture in which the entire protoxin is expressed can be created, but these tissues are typically necrotic or visibly unhealthy and cannot routinely be regenerated into whole plants. This observation may be due to toxic effects of the protoxin or perhaps simply by its insolubility.

SUMMARY OF THE INVENTION

The present invention is summarized in that a chimeric gene construction capable of expression in plant cells includes, in sequence 5' to 3': a promoter sequence effective to initiate transcription in plant cells; a translational enhancer sequence homologous to the transcribed but untranslated sequence immediately preceding the coding region of a plant viral coat protein gene; a coding sequence coding for a protein of less than about 700 amino acids homologous with the amino-terminal portion of *Bacillus thuringiensis* delta-endotoxin; and a polyadenylation sequence.

The present invention is also summarized in that transgenic plants are created which contain such a chimeric gene construction in their genome.

It is an object of the present invention to facilitate the creation of transgenic plants which natively produce enhanced quantities of exogenous proteins.

It is another object of the present invention to create transgenic plants which produce relatively high levels of *Bacillus thuringiensis* delta-endotoxin in their cells so as to have an enhanced resistance to insect predation.

It is a feature of the present invention that cotton plants are created which lessen the need for commonly used pesticides.

Other features, objects and advantages of the present invention will become apparent from the following specification and examples.

BRIEF DESCRIPTION OF THE DRAWINGS

FIG. 1 is a schematic diagram illustrating the steps in the construction of plasmid pTV4 used in an example of the present invention FIG. 2 is a schematic diagram illustrating the steps in the construction of vector pAMVBTS.

FIG. 3 is a schematic diagram illustrating the steps in the construction of the vector pTV4AMVBTSH from the plasmids pTV4 and pAMVBTS.

FIGS. 4A and 4B are together a listing of the believed complete nucleotide sequence of pAMVBTS.

FIG. 5 is a listing of the amino acid sequence of the protein encoded by the coding sequence of pAMVBTS.

DETAILED DESCRIPTION OF THE INVENTION

As will be apparent from the following examples, the present invention arose from the effort to create transgenic plants which express in their cells the *Bacillus thuringiensis* (*B.t.*) delta-endotoxin in such a fashion that the plants cells were toxic to susceptible insect pests when ingested. The introduction of an expressing chimeric gene coding for the expression of the *B.t.* toxin into whole plants proved to be a non-routine procedure, however. Plant tissues in which the full-length mRNA of the introduced gene could be detected tended to be necrotic or at least unhealthy. By making several modifications in the gene construction, whole intact and pathogen resistant transgenic plants were created. These changes included (1) truncating the protoxin coding sequence by deleting a large portion of the carboxy-terminal segment of the protein, (2) stabilizing the remaining carboxy-terminus of the protein by the addition of two terminal proline codons, and (3) adding to the expression cassette, between the promoter and the start of the coding region, a translational enhancer the sequence of which was derived from the transcribed but untranslated leader sequence immediately 5' of the coding region of the RNA of a plant viral coat protein gene. Constructions including these changes were introduced into plant tissues which proved to be readily regenerable. Tobacco and cotton plants regenerated from the transformed tissues exhibited significant mRNA activity and showed high toxicity to Lepidopteran insects in feeding trials.

The theory behind the truncation of the *B.t.* protoxin gene is to cause the expression of a protein toxin in plant cells substantially corresponding to the processed toxin created in the insect gut after proteolysis. The approximate location of the proteolytic site has been previously identified. Schnepf and Whiteley, "Delineation of a Toxin-encoding Segment of a *Bacillus thuringiensis* Crystal Protein Gene," *J. Biol. Chem.*, 260, pp 6273–6280 (1985). The truncation may conveniently be accomplished 3' to that site, located 5' to codon 645 of the published sequence, at any suitable restriction enzyme site.

One possible difficulty arising from the truncation of the *B.t.* toxin coding sequence is that the carboxy-terminus of the truncated expressed protein might be unstable in vivo. To overcome the question of any potential instability, the two codons for the amino acid proline were added to the carboxy-terminus of the truncated coding sequence. The expressed protein therefore possesses two hydrophobic and protease-resistant prolines at its terminus, which may add to the stability of the protein in the cytosol of the plant cells. The resulting protein did prove stable and effective in the plants cells suggesting the success of this strategy.

The strategy behind the addition of the translational enhancer is to increase the translation efficiency of mRNA produced in vivo from the chimeric introduced gene construction. It has been observed that the RNA 4 from alfalfa mosaic virus (AMV), which codes for the coat protein, is efficiently translated both in vivo and in vitro, possibly because of the characteristics of the untranslated region of the RNA located 5' of the coat protein coding sequence. Gehrke et al., "5'-Conformation of Capped Alfalfa Mosaic Virus Ribonucleic Acid 4 May Reflect Its Independance of the Cap Structure or of Cap-binding Protein for Efficient Translation." *Biochem.*, 22, pp 5157–5164 (1983). This observation is consistent with the theory that native or indigenous gene transcriptional and translational systems would naturally evolve to be regulated in order for the organism to control gene activity, while certain viral gene transcriptional and translational systems might evolve to be more efficient, since their success is not dependant on the survival of the other cellular gene and systems. This theory would suggest that viral coat protein genes would be likely to be efficiently translated, since during a phase of viral replication abundant quantities of the components of the replicate viruses must be produced for the virus to maximize its reproduction. Thus, while this strategy is effectuated here by the use of sequence homologous to the 5' untranslated sequence of the RNA of the coat protein gene of AMV, it is believed that other viral coat protein gene systems may have similarly effective translational enhancer sequences.

As with the expression of any other gene product in vivo, a genetic construction to cause expression in plant cells must have appropriate transcription regulatory sequences. The transcription initiation sequence is referred to as a promoter. Several effective promoters are known to be effective in plant cells, most commonly the nopaline synthase promoter from *A. tumefaciens* and the 35S promoter from cauliflower mosaic virus (CaMV 35S), but many other effective promoters in plant cells are known. Transcripts of mRNA are terminated at the 3' end by sequences of polyadenylic acid, enzymatically added post-transcriptionally at the polyadenylation sequence, again of which several are known, such as the polyadenylation sequence from the nopaline synthase gene. Any effective promoter and polyadenylation sequence is believed usable within the present invention. The efficiency of any such promoter is believed to vary somewhat from promoter to promoter (for example CaMV 35S promoter is generally stronger than the nopaline synthase promoter), but is also quite variable in vivo in plants depending on several variables most notable among which is location of gene insertion.

As may be perceived with reference to the following example, the creation of transformed plants may be most conveniently accomplished through the use of a vector which can be readily adapted for the insertion of any specific protein coding sequence. The plant expression vector used here, pTV4AMVBTSH, includes antibiotic resistance markers, T-DNA border fragments, an overdrive sequence, and an expression cassette including a promoter (CaMV 35S), the translational enhancer sequence from AMV, the truncated *B.t.* coding sequence, a sequence including a pair of proline codons and a pair of termination codons, and a transcription polyadenylation sequence, all separated by convenient restriction sites. This vector is thus readily adaptable for use with other proteins by the relatively simple substitution of the new protein coding sequence for the truncated *B.t.* sequence. This substitution can either retain or delete the terminal proline codons depending on the characteristics of the new sequence.

EXAMPLE I

I. Construction of Expression Vector

The present invention has been practiced in an exemplary fashion by the construction and use of plasmid pTV4AMVBTSH, the derivation and construction of which will be discussed below. While specimens of the plasmid, harbored in *E. coli*, have been deposited with the American Type Culture Collection, as described below, the derivation and construction of this plasmid will be discussed in an exemplary fashion here in order to ensure that the construction of this plasmid and the variations thereof envisioned by the present invention will be enabled here. As can be readily seen from the following explanation, many variations in the vector construction are possible while still achieving the beneficial results and advantages intended in the present invention.

The plasmid pTV4AMVBTSH itself is an ampicillin and sulfadiazine resistant plant transformation and expression vector. The actual procedure used by the applicants to construct this vector is not described herein, since the actual series of manipulations used in the evolution of the plasmids which are the predecessors of this vector were considerably more convoluted than necessary to understand how the vector was constructed, how it may be re-created and emulated, and how it functions. The description below does describe, in essence, how the vector was assembled from the various beginning parts and the procedure described here is quite analogous to the procedure by which the vector was actually constructed by the applicants here. The beginning parts and the ending results are all identical to that utilized by the applicants and the methods and procedures are similar, although not identical.

The plasmid pTV4AMVBTSH is a co-integrate of a sulfadiazine resistant plasmid pTV4 and an ampicillin resistant plasmid pAMVBTS. How each of these constituent plasmids may be constructed is what is described first below. The plasmid pAMVBTS is a small plasmid vector, capable of replication in *E. coli*, which contains a plant-expressible gene cassette that contains as its coding region a truncated section of the *B.t.* toxin coding sequence. The plasmid pTV4 is a plant transformation cassette vector containing left and right border sequences useful for Agrobacterium-mediated plant transformation and a synthetic overdrive sequence, as will be discussed below. How each of these two vectors may be constructed is described below, beginning with pTV4.

II. Construction of pTV4

The plasmid pTV4 is a derivative of pCMC92 which was constructed to serve as a carrier plasmid in a binary vector plant transformation system. The vector pCMC92 consists of a plasmid replicon derived from pRSF1010, the left and right T-DNA border regions of Ti plasmid T37 (designated LB and RB in FIG. 1), and a chimeric selectable marker conferring kanamycin resistance on transformed plant cells. The chimeric selectable marker includes the coding region for the enzyme aminoglycoside-phosphotransferase (3')-II ("APH-II") preceded by the promoter from the nopaline synthase gene from *A. tumefaciens* (NosPr) and followed by the polyadenylation sequence from the same gene (NospA). The plasmid pCMC92 also carries a selectable marker gene of sulfadiazine resistance, designated Su$^R$ in FIG. 1, located outside of the T-DNA borders. Samples of vector pCMC92 are on deposit and available from the American Type Culture Collection as described below.

In order to derive pTV4 from pCMC92 a series of alterations must be made to pCMC92. These alterations include the deletion of restriction sites at the 3' end of the APH-II gene, inside of the left T-DNA border, and substitution for the natural sequence right T-DNA border region on pCMC92 with a synthetic DNA fragment containing both an artificial right T-DNA border and an overdrive region of a Ti plasmid. These alterations will be described in sequence below and are schematically illustrated in FIG. 1.

II.a. pTV4 Construction—Deletion of 3' Sites

The vector pCMC92 has a polylinker region, consisting of a series of closely adjacent restriction sites, immediately inside the T-DNA left border region (LB). This polylinker in pCMC92, beginning closest to the left border and proceeding toward the APH-II coding region, has the restriction sites Sma I, BamH I, Xba I, and Sal I in order. It is desired to delete the sites. To carry out this deletion, the Sma I site may be converted to an Xho I site by digestion, first with Sma I, to generate blunt ends which are then ligated with commercially available Xho I linker fragments and transformed into E. coli. The plasmids having the appropriate conversion would then have a polylinker which consists, in order, of Xho I, BamH I, Xba I and Sal I. Because Xho I and Sal I leave identical sticky ends on the DNA sequences which they cleave, this enables a ligation of the two sites that results in the loss of recognition of the ligated DNA region by either enzyme. Thus this intermediate plasmid, designated pCMC92X in FIG. 1, is digested completely with both Xho I and Sal I. The resulting linear sequence can be ligated, to close the plasmid, and then digested with either Xho I or Sal I to linearize any plasmids that do not ligate with the Sal I sticky end to the Xho I sticky end. The resulting constructs can then be transformed into E. coli and selected for sulfadiazine resistance. The resulting plasmid, designated pCMC92XD in FIG. 1, will have lost the polylinker region containing the Xba I and BamH I sites, and the Xho I and Sal I sites will have been destroyed in the ligation. The resulting plasmid pCMC92XD will have no restriction sites for Xho I, Sal I, or Bam HI. One remaining Xba I site exists, between the APH-II coding sequence and the nopaline synthase promoter, and adjacent to it is a unique Hind III site. It is then appropriate to delete both of these sites.

II.b. pTV4 Construction—Deletion of 5' Sites

To remove the adjacent Hind III and Xba I sites on vector pCMC92XD, the plasmid pCMC92XD can be digested to completion with both Hind III and Xba I. The sticky ends resulting from each of these digestions can then be removed by digestion with mung bean nuclease followed by treatment with Klenow polymerase and all four deoxynucleotide triphosphates, to create ends that are blunt. The blunt ends may then be ligated together using T4-DNA ligase, which will close this plasmid, which can then be recovered by transformation in E. coli and selection for sulfadiazine resistance. The resulting plasmid, designated pCMC92XD2 in FIG. 1, will have lost both the Hind III and Xba I sites.

II.c. Construction of pTV4 —Addition of Right Border

The DNA sequence which is 5' from the APH-II coding sequence on pCMC92XD2 consists of the nopaline synthase promoter (NosPr) and adjacent plasmid nucleotides derived from pTiT37 from A. tumefaciens. This adjacent DNA encodes the right border region of the T-DNA (RB) and an associated sequence which has been designated as an "overdrive" sequence. Peralta et al., "Overdrive, a T-DNA Transmission Enhancer on the A. Tumefaciens Tumor-Inducing Plasmid," *EMBO Journal*, Vol. 5, pp 1137–1142 (1986). To convert pCMC92XD2 to pTV4, the region of pCMC92XD2 between a Sac II site located immediately 5' of the nopaline synthase promoter and a unique Eco RI site located approximately 1 kilobase outside of the right border T-DNA sequence must be deleted. The deleted nucleotide sequence is replaced with a synthetic oligonucleotide corresponding to the T-DNA border and a consensus overdrive sequence. This can be conveniently accomplished in a series of three steps.

First, a synthetic right border region can be substituted for the region of pCMC92XD2 between the Sac II and Eco RI sites noted above. This substitution can be accomplished by conducting a complete digestion of pCMC92XD2 with Eco RI followed by a partial digestion with Sac II and purification of linear fragments that have lost the region of the Ti plasmid referred to above. This linear plasmid should be easily distinguished on agarose gels from plasmids that are cut at the alternative Sac II site, or plasmids that did not get cut at either Sac II site, by size. The purified deleted DNA can then be combined with a synthetic duplex DNA fragment, corresponding to the Ti plasmid right border, which can be formed by annealing two synthetic complimentary oligonucleotides. The two synthetic nucleotides are shown below in their form annealed to form a duplex DNA linker. The two oligonucleotides are synthesized to include sticky Sac II and Eco RI ends after annealing.

```
         Sac II  Cla I Hind III            - - TI   RIGHT   BORDER- -   Kpn I Eco RI
    5'-    GGCATCGATGAAGCTTTGACAGGATATATTGGCGGGTAAACGGTACCG      -3'
           : : : : : : : : : : : : : : : : : : : : : : : : : : : : : : : : : : : : : : : : : : : : : :
    3'-CGCCGTAGCTACTTCGAAACTGTCCTATATAACCGCCCATTTGCCATGGCTTAA-5'
```

After the plasmid which results has been transformed into E. coli and selected for sulfadiazine resistance, the construction of this plasmid, designated pTV2, can be confirmed by restriction digests, including a digest for the newly introduced restriction sites for Cla I, Hind III and Kpn I which are noted in the sequence for the synthetic fragment illustrated above, as well as in FIG. 1. In FIG. 1, the restriction sites are indicated as well as the T-DNA border region, designated Syn. RB.

II.d. Construction of pTV4 —Conversion of Cla I to Xho I

The next operation is to provide an insertion site for the cointegration of plasmids containing either a unique Xho I site or a unique Sal I site (since these two enzymes have compatible sticky ends). To do this, the newly-introduced Cla I site is converted to an Xho I site through the use of commercially available Xho I linkers. The Cla I site of the sequence shown above is not subject to dam methylation, a typical methylation characteristic of *E. coli*. This site is the only Cla I site on pTV2 that will digest when the DNA is dam-methylated. Therefore, if the plasmid is digested to completion with Cla I, the sticky ends may be filled in with Klenow polymerase, and the appropriate four deoxynucleotide triphosphates, and then the appropriate commercially available synthetic linkers may be added by blunt-end ligation. Following appropriate digestions and ligations of the Xho I linkers, and transformation of *E. coli* followed by selection for sulfadiazine resistance, plasmids can be isolated in which the Cla I site is converted to what will now be a unique Xho I site on the resulting plasmid, designated pTV3 in FIG. 1.

II.e. Construction of pTV4 —Addition of Overdrive

To complete the construction of pTV4, a synthetic overdrive consensus sequence is added to pTV3, as illustrated in FIG. 1. This sequence is chosen to correspond to the homologous regions of various infective Ti plasmids. The selected consensus sequence is as follows:

```
      Kpn I              overdrive              Eco RI
5' -       CTTTGT ATGTTTGTTTGTTTGTTTG            -3'
           : : : : : : : : : : : : : : : : : : : : : : : : : : :
3' - CATGGAAACATACAAACAAACAAACAAACTTAA -5'
```

The two oligonucleotides synthesized to form the above duplex sequence provide, after hybridization, for Kpn I and Eco RI sticky ends following annealing. To insert this duplex sequence into the plasmid, pTV3 is digested with Kpn I and Eco RI, each of which has a unique restriction site on the plasmid pTV3 separated by a short oligonucleotide. The plasmid DNA is then combined for ligation with the synthetic nucleotide sequence, provided in excess in order to preferentially replace any residual oligonucleotide resulting from digestion of pTV3 with Kpn I and Eco RI. Transformation of *E. coli* with the ligated DNA, followed by repeated selection for sulfadiazine resistance, results in the isolation of pTV4, which may be confirmed by restriction mapping and sequencing of the synthetic region. The completed pTV4, as illustrated in FIG. 1, consists of an RSF1010 replicon with an authentic T-DNA left border region from pTiT37 (LB), a chimeric APH-II gene constructed with a nopaline synthase promoter (NosPr) and a nopaline synthase polyadenylation region (NospA), a plasmid unique Xho I site, a synthetic T-DNA right border fragment that corresponds to the sequence found in the pTiT37 right border (Syn. RB), and a synthetic consensus overdrive sequence (Syn. OD). The unique Xho I site on pTV4 can be used as an insertion site for co-integration with other plasmids, and the DNA inserted in this fashion would be inside the right T-DNA border and would be expected to be transferred into plants during Agrobacterium-mediated transformations.

III. Construction of pAMVBTS

The vector pAMVBTS consists of an ampicillin resistance (Ap$^R$) plasmid replicon derived from pMT21, containing a chimeric gene construction which consists of, in order from the 5' end, a DNA fragment corresponding to the cauliflower mosaic virus 35S transcriptional promoter (CaMV 35S), a DNA leader fragment corresponding to the alfalfa mosaic virus coat protein mRNA 5' noncoding region (AMV), a DNA fragment corresponding to the amino-terminus of the *Bacillus thuringiensis* delta-endotoxin (*B.t.*), and a DNA fragment corresponding to the polyadenylation region of nopaline synthase (NospA). Each of these component parts is conveniently separated from the others by vector-unique restriction sites. Two approaches are described herein for the construction of this plasmid. One approach describes how the plasmid can be constructed from previouly known or previously deposited components. The second approach illustrates how the plasmid pTV4AMVBTSH, also now deposited, can be used to derive the vector pAMVBTS.

The construction of the vector pAMVBTS from prior constituent parts begins with a plasmid pCMC1022, which is an ampicillin resistant (Ap$^R$) plasmid vector derived from pMT21 that includes a plant-expressible gene cassette encoding for the expression of the APH-II gene derived from Tn5. The gene cassette contained in pCMC1022 consists of, from 5' to 3', a promoter which is the CaMV , 35S promoter, the APH-II coding region of Tn5 (APH-II), and the polyadenylation region of nopaline synthase(NospA). This plasmid can be modified to create pAMVBTS by a series of modifications which are intended to: shorten the DNA sequence used as the transcriptional promoter, add after the promoter a DNA sequence which encodes a 5' nontranslating RNA leader from the alfalfa mosaic virus coat protein, replacing the APH-II coding region with a truncated *B.t.* toxin coding region, and adding two proline codons to the original amino acids located at the site of toxin truncation.

Figure 2:
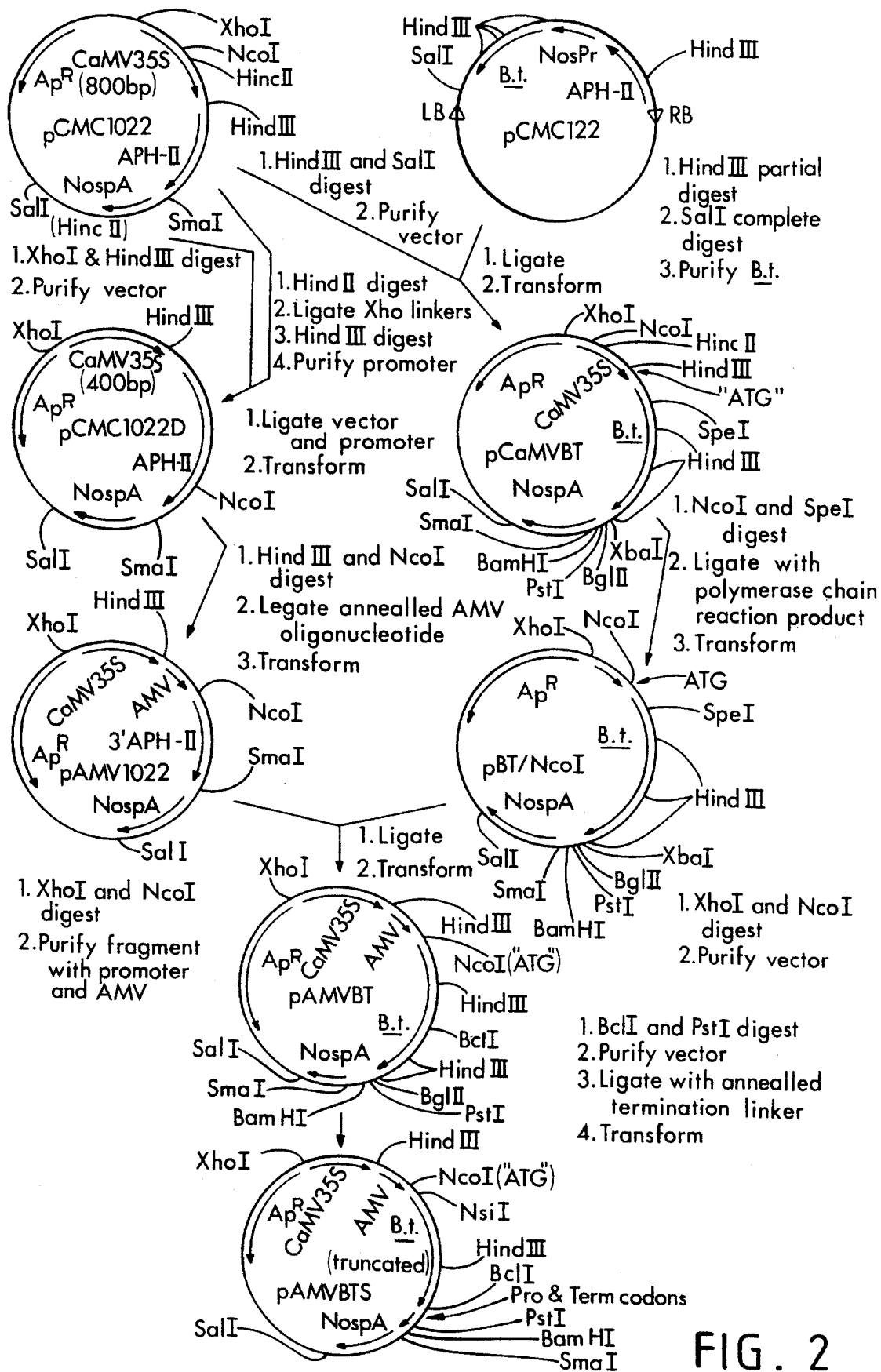

The steps in the construction of pAMVBTS are illustrated in schematic fashion in FIG. 2.

III.a. Construction of pAMVBTS—Promoter Modification

The transcriptional CaMV 35S promoter present on pCMC1022 is derived from approximately 800 base pairs of DNA nucleotides derived from the cauliflower mosaic virus. At the 5' end of the fragment on pCMC1022 is an Xho I site previously placed there using commercial Xho I linkers, while at the 3' end of the promoter fragment, immediately beyond the proposed start of transcription activity in plants, is a Hind III site also resulting from previous ligation with commercially available Hind III linkers. The total length of the promoter DNA, between the Xho I site and the Hind III site on pCMC1022, is about 786 nucleotides. In the construction of pAMVBTS, several hundred nucleotides of non-essential non-translated DNA are removed from the DNA derived from the cauliflower mosaic virus, all located 5' to the transcriptional promoter sequence. This is accomplished by digesting pCMC1022 with Xho I and Hind III followed by purification of the double-digested vector away from the 786 nucleotide fragment containing the CaMV 35S promoter. A separate promoter fragment, for later ligation with the double-digested vector, is prepared by digesting separately pCMC1022 with Hinc II, which recognizes a restriction site located approximately 423 nucleotides 5' to the Hind III site, and which leaves a blunt end on the fragment. Commercially available Xho I linkers are kinased, then ligated to the blunt end created by Hinc II. The ligation is followed by digestion with Xho I to expose an Xho I compatible sticky end. This DNA is then digested with Hind III, resulting in an approximately 428 nucleotide CaMV 35S promoter fragment with Xho I and Hind III sticky ends, which may be purified on agarose gel for use in ligation with the above mentioned double-digested vector. The Xho I/Hind III-digested vector is then combined with the 428 base pair promoter fragment, and the two fragments are ligated together. The resulting construction can be transformed into *E. coli* and selection carried out for ampicillin resistant transformants. The structure of the correct plasmid, designated pCMC1022D in FIG. 2, may be confirmed by miniprepping the colonies and conducting appropriate restriction digests, followed by sequencing of the region where the Xho I linkers were added. The resulting plasmid, pCMC1022D, is identical to pCMC1022 except for a deletion of approximately 363 base pairs of DNA derived from the cauliflower mosaic virus which is located 5' to the transcriptional promoter on pCMC1022.

II.b. Construction of pAMVBTS—AMV Leader

Because viral coat proteins are known to be efficiently translated both in vivo and in vitro, the 5' noncoding region of the alfalfa mosaic virus (AMV) coat protein mRNA was selected as the leader sequence to be transcribed in the chimeric gene constructed for this vector. To construct a gene encoding the AMV leader, two complimentary oligonucleotides were synthesized. The two oligonucleotides produced may be annealed easily by combining equimolar quantities of the two oligonucleotides at a concentration of approximately 10 to 50 micrograms per milliliter total DNA, heating the mixture in low salt (10 mM Tris-HCl, pH 8, 10 mM MgCl$_2$) to 90 degrees for 10 minutes, followed by gradual cooling to room temperature. If done in this fashion, the oligonucleotides efficiently anneal and have a duplex structure and sequence as follows, with a Hind III sticky end at the 5' end and an Nco I sticky end at the 3' end of the fragment, when oriented as shown below.

```
Hind III                                      Nco I
5'-AGCTTTTTATTTTTAATTTTCTTTCAAATACTTCCAC      -3'
   : : : : : : : : : : : : : : : : : : : : : : : : : : : : : : : : : :
3'-     AAAATAAAAATTAAAAGAAAGTTTATGAAGGTGGTAC -5'
```

To prepare the DNA vector pCMC1022D for joining to the oligonucleotide fragment, pCMC1022D is digested with Hind III plus Nco I and the approximately 2.5 kilobase vector is purified by electrophoresis away from the approximately 580 base pair fragment corresponding to the amino-terminal portion of the APH-II coding region. The Nco I site is located intermediate in the APH-II coding region, leaving only the 3' portion of the APH-II gene, designated 3'APH-II in FIG. 2, in the vector. The approximately 2.5 kilobase vector fragment is then combined with the annealed oligonucleotide and ligation is carried out. The resulting DNA is transformed into *E. coli* and selected for ampicillin resistant colonies. Minipreps may be conducted to determine that the desired plasmid, designated pAMV1022 in FIG. 2, has been obtained. DNA sequencing may be conducted to ascertain that the AMV oligonucleotide has the correct sequence. The plasmid pAMV1022 now includes a promoter cassette which is bordered at its 5' end by an Xho I site and at its 3' end with an Nco I site. This promoter cassette includes approximately 400 base pairs of the CaMV 35S promoter DNA (CaMV 35S) followed by the approximately 35 base pairs of the oligonucleotide homologous to the AMV RNA leader sequence (AMV). Transcription activity in plants, based on analysis of the CaMV promoter, is believed to initiate immediately 5' to the Hind III site joining the CaMV sequence to the AMV leader sequence. To prepare this promoter cassette for additional constructions, pAMV1022 is digested with both Xho I and Nco I, and the approximately 466 base pair fragment is purified from the remaining plasmid using agarose gel electrophoresis. This fragment will be used further in the construction of pAMVBT described below.

II.c. Construction of pAMVBTS—*B.t.* Toxin Gene

The entire coding region for the *B.t.* delta-endotoxin has been previously characterized, published, and made available through deposits. See U.S. Pat. Nos. 4,448,885 and 4,467,036 and Schnepf et al., "The Amino Acid Sequence of a Crystal Protein from *Bacillus thuringiensis* Deduced from the DNA Base Sequence," *J. Biol. Chem.*, 260, pp. 6264–6272 (1985). A modification of the amino-terminal coding region of the DNA fragment which encodes the toxin has been made to establish a Hind III site by mutagenesis immediately preceeding the initiator "ATG" of the toxin coding region. An available deposited plasmid containing the *B.t.* delta-endotoxin coding region with this mutagenic modification is plasmid pCMC122, deposited with the ATCC Accession Number 39639. The following discussion illustrating the construction of a toxin coding region as it is used in pAMVBTS begins with the plasmid pCMC122. Alternatively, an almost identical process can be utilized beginning with the vector pSYC823, also deposited with the American Type Culture Collection Accession Number 39657.

III.d. Construction of pAMVBTS—Clone *B.t.* into pCMC1022

The vector pCMC122 is a plant transformation vector containing within it an expression cassette which consists of a *B.t.* protoxin coding region (*B.t.*) bracketed by a nopaline synthase promoter (NosPr) and a nopaline synthase polyadenylation region (NospA) located between T-DNA border regions (LB and RB). In order to utilize this DNA construct, the amino acid coding region of the protoxin and the associated nopaline synthase polyadenylation region are excised from pCMC122 and inserted into pCMC1022. First, pCMC122 is partially digested with Hind III. There are several Hind III sites on the plasmid, but the only site that is useful is the site immediately adjacent to the "ATG" initiation codon of the *B.t.* coding region. The other three additional Hind III sites are located within the coding sequence itself for the *B.t.* protoxin gene. A partial digest intended to segregate the appropriately cut vector is conveniently accomplished by digesting 100 micrograms of pCMC122 with 10 units of Hind III as recommended by the supplier, but terminating 20% of the reaction at 5 minute intervals by removing aliquots and combining with phenol beginning 5 minutes after initiation of the reaction. The 5 aliquots are then separated from the phenol, pooled, ethanol precipitated, and washed with 70% ethanol, after which they are resuspended for a complete digestion with Sal I. This reaction mixture is then subjected to preparative agarose gel electrophoresis and the approximately 4.0 kilobase fragment corresponding to the entire *B.t.* protoxin coding region plus the nopaline synthase polyadenylation region may be excised from the gel and recovered. This fragment will have a Hind III site at the 5' end of the coding region and a Sal I site at the 3' end of the fragment. To prepare an appropriate vector to receive this coding region construction, pCMC1022 is cleaved in a complete digestion with Hind III and Sal I and the approximately 2660 base pair vector fragment is gel purified. This process is again illustrated in FIG. 2. The digested pCMC1022 vector is then combined in equimolar amounts with the purified *B.t.* protoxin coding region from pCMC122 and ligation is carried out. Following transformation into *E. coli* and selection for ampicillin resistance, the correct plasmid structure of the resulting plasmid, designated pCaMVBT in FIG. 2, can be confirmed by minipreps. The resulting vector pCaMVBT represents an expression plasmid containing, in sequence, an 800 base pair CaMV 35S promoter fragment (CaMV 35S), the complete *B.t.* protoxin coding region (*B.t.*), and a nopaline synthase polyadenylation region (NospA).

III.e. Construction of pAMVBTS—Modification of Amino Terminus of Toxin Gene

In order to improve the utility of the vector containing the *B.t.* protoxin coding sequence for use in pAMVBTS, the DNA sequence immediately upstream to the "ATG" initiation codon was altered to include a restriction site for the endonuclease Nco I. This sequence is CCATGG, wherein the internal "ATG" represents the initiation methionine codon of the toxin protein coding sequence. This may be done by chemically synthesizing two oligonucleotide primers with regions of homology to the amino terminus of the toxin coding region and amplifying a DNA fragment corresponding to a modified amino-terminal coding region utilizing the polymerase chain reaction (PCR). Nucleotides 5 to 25 of the first nucleotide, designated KB15 and illustrated below, were homologous to nucleotides 1 to 21 of the toxin coding region, beginning the numbering of the nucleotides of the coding region with the "A" of the initiation codon. This represents nucleotides 527 to 547 of the published toxin sequence as published by Schnepf et al. above. The third through eighth nucleotides of KB15 include the recognition sequence for the endonuclease Nco I, with the first two nucleotides of KB15 serving a stabilizing role in both the polymerase chain reaction amplification sequence and during subsequent cleavage of the amplified DNA fragment with the endonuclease Nco I. The second oligonucleotide, designated KB16 and also shown below, is homologous to the opposite or "antisense" strand of the toxin coding region at nucleotides 722 to 701 of the published sequence. These two oligonucleotides were used in conjunction with the DNA encoding the *B.t.* protoxin that is found on pCaMVBT, described above, in a polymerase chain reaction essentially as described in the published description of the polymerase chain reaction protocol. Saiki et al. "Enzymatic Amplification of Gamma-Globin Genomic Sequences and Restrictions Site Analysis for Diagnosis of Sickle Cell Anemia," *Science*, Vol. 230, pp 1350–1354 (1985). Details of this reaction are also provided below.

KB15 25mer 5'- CGCCATGGATAACAATCCGAACATC -3'

KB16 22mer 5'- CCCATATTATATCAACTAGTCC -3'

To amplify the modified amino-terminal fragment of the *B.t.* protoxin encoding gene from pCAMVBT, a hundred microliter reaction is prepared containing 10mM Tris-HCl (pH 7.5), 50 mM NaCl, 10 mM $MgCl_2$, 1.5 mM of each of the four dNTP's, 0.01 microgram of pCaMVBT and 2 micrograms each of KB15 and KB16 described above. This reaction is heated to 100 degrees C for 2 minutes, microfuged at room temperature for 30 seconds, and then 1 microliter of Klenow fragment DNA polymerase (U.S. Biochemicals, 5 units per microliter) is added and mixed into the reaction. The first cycle of the polymerase chain reaction is conducted by incubating this mixture for 2 minutes at 37 degrees, then 2 minutes at 100 degrees, followed by 30 second microcentrifugation. An additional microliter of Klenow polymerase is then added to initiate the second cycle of the polymerase chain reaction and a subsequent series of cycles of 37 degrees, 100 degrees, centrifugation, and polymerase addition are continued until 20 synthesis steps at 37 degrees have been conducted. After the twentieth cycle of synthesis at 37 degrees, the reaction is heated only to 65 degrees for 10 minutes to inactivate the Klenow polymerase. The reaction products are then returned to 37 degrees, brought to 100 mM NaCl, and 50 units each of Nco I and Spe I are added. Incubation is then conducted at 37 degrees for 1 hour, and the reaction mixture is subject to electrophoresis on 3% Nusieve agarose.

The amplified 178 nucleotide fragment with exposed Nco I and Spe I sticky ends, which corresponds to nucleotides 481 to 657 of the pAMVBTS plasmid, is purified by electroelution from the agarose after excision of the ethidium bromide-stained band from the gel. This amplified fragment is cloned into a plasmid vector prepared from pCaMVBT. For this reaction, pCaMVBT was digested with Nco I and Spe I and the larger of the two resulting fragments gel-purified. Spe I cuts the vector pCaMVBT only near the amino terminus of the *B.t.* protoxin coding region. Nco I also cuts pCaMVBT at a unique site, at nucleotide number 272 within the CaMV DNA fragment. Thus the combination of these two enzymes results in deletion of a functional portion of the CaMV 35S promoter fragment, so that the resulting plasmid following cloning of the polymerase chain reaction-amplified toxin amino-terminus is not capable of expression in plant cells, due to lack of a promoter. The amplified DNA fragment and the Nco I and Spe I double-digested vector are combined and ligated, and transformed into *E. coli* which is then subjected to selection for ampicillin resistance. The resulting plasmid, designated pBT/NCOI in FIG. 2, consists of a fragment of the CaMV DNA terminating at the unique Nco I site, the *B.t.* protoxin coding region with a modified amino-terminus consisting of the Nco I restriction site, and a nopaline synthase polyadenylation region. The amplified region between Nco I and Spe I are sequenced to confirm that the correct DNA has been amplified.

III.f. Construction of pAMVBTS—Combining pAMV1022 with pBT/NCOI

In order to insert a transcriptional promoter onto pBT/NCOI, and to combine with the upstream AMV leader sequence, the coding region from pBT/NCOI must be combined with pAMV1022. The vector pBT/NCOI is digested with Nco I and Xho I, and the larger component containing the vector may be purified by agarose gel electrophoresis, followed by electroelution. The plasmid pAMV1022 is digested with Xho I and Nco I followed by purification to obtain the 466 base pair promoter fragment from the remaining portion of the vector. The two purified DNA fragments are then combined, ligated, and transformed into *E. coli* which is then selected for ampicillin resistance. The resulting plasmid, designated pAMVBT in FIG. 2, is confirmed by plasmid minipreps. The expression cassette in the plasmid pAMVBT consists of a functional CaMV 35S promoter of approximately 430 base pairs (CaMV 35S), a 35 nucleotide DNA fragment encoding the AMV coat protein noncoding region (AMV), a complete coding sequence for the *B.t.* protoxin (B.t.) and followed by the polyadenylation region from nopaline synthase (NospA).

III.g. Construction of pAMVBTS—Truncation of Toxin Region

It has previously been demonstrated that only the amino-terminal portion of the B.t. protoxin is required for toxicity. Schnepf and Whiteley, "Delineation of a Toxin-Encoding Segment of a *Bacillus thuringiensis* Crystal Protein Gene," *J. Biol. Chem.*, 260, pp. 6273–6280 (1985). Deletion of the carboxyl-terminal portion of the toxin sequence beyond a recognition site for the endonuclease Bcl I (a sequence of TGATCA, nucleotides 2413–2418 of the vector pAMVBTS, FIG. 4, and nucleotides 2458–2463 of the published toxin sequence), located in amino acid codon 644 of the protoxin sequence, removes a significant portion of the protoxin but does not eliminate toxicity. Deletion of the coding sequence beyond the Bcl I site and codon 644 does remove at least 1594 nucleotides from the expected mRNA (depending on how the deletion is accomplished) and eliminates 45% of the total amino acids found on the protoxin. While it is possible that stabilizing structures may be located on the carboxy-terminal portion of the protoxin coding sequence, or at the 3' terminus of the bacterial transcribed mRNA, there i s no apparent requirement for the retention of the carboxy-terminal portion of the protoxin when expressed in plants. In fact, to the contrary, an increase in efficiency of expression in plants might be expected by removal of some of the sequences from the chimeric genes since then both the transcribed mRNA and the translated protein would be proportionately smaller and less complex. Furthermore, any functions of either the carboxy-terminal portion of the protoxin or the 3' terminus of the mRNA that are deleterious to plant cell growth or activity would be eliminated by removal of these terminal sequences. Because the carboxy-terminus of the protoxin is believed to be involved in the formation of the crystal structure when the protoxin is expressed in *B. thuringiensis*, and may serve a similar function in the cells of plants expressing the protoxin, removal of this portion of the protoxin may additionally eliminate deleterious effects on plant cell growth or activity caused by the insolubility of the protoxin crystal structure.

The plasmid pAMVBT has two Bcl I restriction sites located within the coding region of the protoxin. The site which is most 5', corresponding to nucleotide 2413 of pAMVBTS, FIG. 4, is the site mentioned above as being just outside the necessary coding sequence for toxicity. The second site, which is not the desired one, is located further along the protoxin coding sequence. The vector pAMVBT also has unique Pst I site, located in the polylinker region between the nopaline synthase polyadenylation region and the termination of the protoxin sequence. This site is located at nucleotide 2432 of the pAMVBTS sequence illustrated in FIG. 4. To truncate the protoxin region, to eliminate the portion not required for toxicity, the coding region of the protoxin in pAMVBT is truncated by deletion of all the DNA between the most 5' Bcl I site and the Pst I site. Into the location of this deleted DNA a synthetic DNA duplex linker is inserted as illustrated below.

```
       BclI                            PstI
5'- GAT CAA CCA CCT TAA TAG CTG CA -3'   KB19
    : : : : : : : : : : : : : : :
3'-     TT GGT GGA ATT ATC G        -5'  KB20
    asp gln pro pro ter ter
```

(pro = proline codon; ter = termination codon)

As can be seen, the duplex linker is formed by annealing two oligonucleotides, designated KB19 and KB20. These nucleotides are designed to restore both the Bcl I site of the original B.t. toxin coding sequence and the Pst I site joining the toxin coding region to the polyadenylation region when cloned into the above described Bcl I/Pst I deletion plasmid. Because the Bcl I site is located within the coding region for the protoxin, the linker formed from oligonucleotides KB19 and KB20 was further designed to terminate the protein coding region with the addition of two new adjacent termination codons, those being the TAA and TAG sequences in the above synthetic linker. These terminations codons are appropriate because of the lack of termination codons located at this position in the truncated gene coding sequence. In addition, to stabilize the carboxy-terminus of the truncated toxin protein, upstream of the two termination codons, two additional codons for the amino acid proline, CCA and CCT, were included in the linker as carboxy-terminal codons before the termination codons.

Construction of the truncated toxin expression cassette was carried out by first digesting the plasmid pAMVBT with Bcl I and Pst I to delete the carboxy-terminus of the B.t. protoxin coding region. The DNA for this reaction was prepared from an *E. coli* strain free of dam methylase, which methylates the "A" in the sequence "GATC," since methylation at this site inhibits cleavage by the endonuclease Bcl I. The remaining approximately 4564 base pair fragment is then purified by agarose gel electrophoresis. The oligonucleotides KB19 and KB20 are chemically synthesized in the sequence shown above, annealed, and then are combined with the digested vector. It is unnecessary to phosphorylate the synthetic linkers with polynucleotide kinase, since ligation of the plasmid vector with the 3' ends of the unphosphorylated linkers occurs with sufficient efficiency and repair of the unligated 5' end occurs following transformation in *E. coli*. However, it is acceptable to phosphorylate the linkers if care is then used to avoid polymerization of the linkers without ligation to the vector. After transformation of this ligation into *E. coli* and selection for ampicillin resistant colonies, plasmid minipreps can then be done to confirm that the correct plasmid has been obtained, pAMVBTS. Sequencing of the synthetic DNA sequence should be carried out to confirm the correct coding sequence has been cloned. The coding cassette of the resulting plasmid pAMVBTS consists, in 5' to 3' sequence of: the CaMV 35S promoter (CaMV 35S), free of unnecesssary 3' DNA, DNA encoding an mRNA leader homologous to the AMV coat protein mRNA 5' nontranslating region (AMV), DNA encoding a truncated B.t. toxin (B.t.) with an Nco I site at the "ATG" initiator and 2 proline codons immediately preceding two new termination codons (Pro & Term) and terminated by a Pst I site, and the polyadenylation region of nopaline synthase (NospA).

The believed complete nucleotide sequence of the vector pAMVBTS is illustrated in FIGS. 4A and 4B. The references above to the sequence position on that vector match the reference locations indicated in FIG. 4. The sequence of FIGS. 4A and 4B is believed correct, and was determined partially from published sequence of the beginning vectors and partially from sequencing data and thus consequently may have minor base pair errors not affecting its successful function or use.

Figure 3:
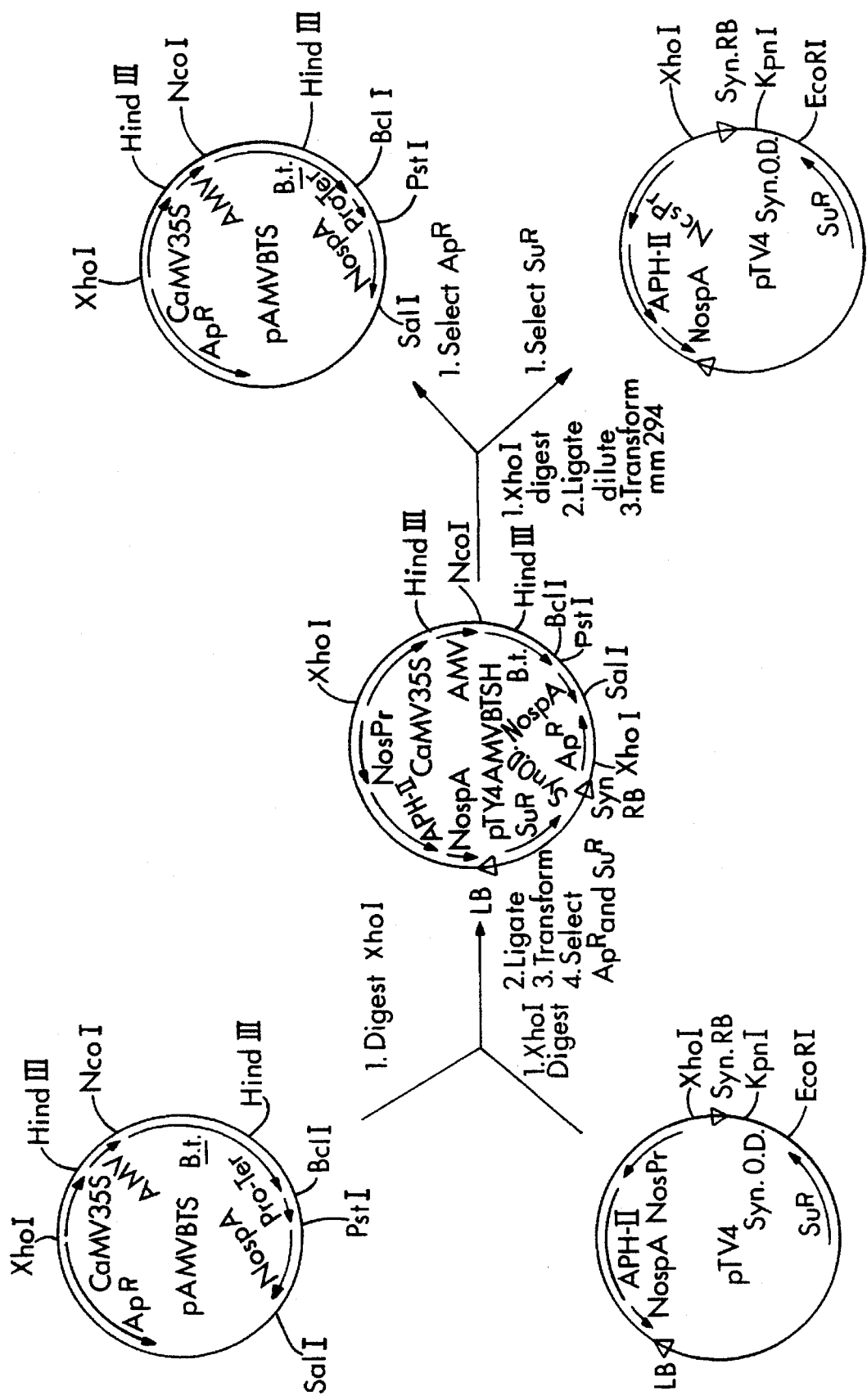

In the sequence of FIGS. 4A and 4B, nucleotide 1 begins at an EcoRI side just 5' to the unique Xho I site. The Xho I site shown in FIGS. 2 and 3 may be found at nucleotides 16 to 21 of the sequence in FIGS. 4A and 4B.

Shown in FIG. 5, is a listing of the amino acid sequence of the protein coding region of pAMVBTS (and pTV4AMVBTSH). The listing uses the following standard one-letter abbreviations: A-Alanine; R-Arginine; N-Asparagine; D-Aspartic Acid; C-Cysteine; Q-Glutamine; E-Glutamic Acid; G-Glycine; H-Histidine; I-Isoleucine; L-Leucine; M-Methionine; F-Phenylalanine; P-Proline; S-Serine; T-Threonine; W-Tryptophan; Y-Tyrosine; and V-Valine. This listing is but an example of the several homologous B.t. amino-terminus amino acid sequences.

IV. Construction of pTV4AMVBTSH

The plant expressible B.t. expression vector pTV4AMVBTSH results from cointegration of plasmids pTV4 and pAMVBTS described above, as illustrated in FIG. 3. The two progenitor plasmids pTV4 and pAMVBTS are first each digested with endonuclease Xho I which cleaves each of the plasmids at a unique site. The linearized plasmids are then cleaned by phenol extraction and ethanol precipation, combined for ligation using T4 DNA ligase, and transformed into *E. coli* host MM294. Selection was then applied to the transformed *E. coli*, for both ampicillin resistance and sulfadiazine resistance, and plasmid cointegrates were analyzed by minipreps. The resulting plasmids are of two different types, depending on the relative orientation of the two cointegrated vectors. Where the vectors integrate in the orientation shown for pTV4AMVBTSH illustrated in FIG. 3, in which the direction of transcription of the ampicillin resistance gene ($Ap^R$) from pAMVBTS is the same as the direction of transcription of the sulfadiazine resistance gene ($Su^R$) from pTV4, there are no directly repeated DNA sequences that can generate homologous deletions in *E. coli*, *Agrobacterium*, or in plant cells. In plasmids having the opposite orientation of the cointegration, the nopaline synthase polyadenylation regions (NospA) would be in direct repetition and would therefore be capable of deleting the APH-II gene in vivo by homologous recombination. In addition, the enhancer region at the 5' end of the CaMV 35S promoter is situated directly adjacent to the nopaline synthase gene from pTV4 and would therefore be likely to stimulate that gene as well as the *B.t.* toxin gene in the selected orientation for pTV4AMVBTSH.

V. Construction of pTV4 and pAMVBTS from pTV4AMVBTS

Plasmid pTV4AMVBTSH has been deposited with the American Type Culture Collection, Accession No. 53636. Since this plasmid is a cointegrate of the two progenitor plasmids pTV4 and pAMVBTSH which were opened at unique sites for the restriction endonuclease Xho I, it may readily be used to regenerate both of those two progenitor plasmids. This is the second, and much easier method now, for creating pAMVBTS or derivatives thereof. If DNA of pTV4AMVBTSH is digested with Xho I to completion, then phenol extracted and ethanol precipitated to clean it, the DNA may then be resuspended as recommended for ligation by suppliers of T4-DNA ligase, but by maintaining the DNA at a dilute concentration, about 10 micrograms per mililiter, ring closure is favored over cointegration. The resulting structures can be transformed into *E.coli* MM294 or any other suitable strain. By appropriate selection among the transformation progeny the colonies which were only ampicillin resistant will be found to contain pAMVBTS, while the colonies only sulfadiazine resistant will contain pTV4. Thus, as illustrated in FIG. 3, the vector pTV4AMVBTSH can be readily resolved into its progenitor vectors which can be readily recombined to create the plant expressible vector.

While these vectors are particularly suitable for the expression of the *B.t.* toxin protein in plant cells, they may also be utilized for the expression of other gene products in plant cells. Note that the *B.t.* coding region in pAMVBTS (or pTV4AMVBTS) is neatly contained between a unique Nco I site and a downstream unique Pst I site. Thus the coding region can readily be excised from pAMVBTS and any other appropriate coding region can be inserted therefor. The insertion of any alternate coding sequence in this region would take full advantage of the upstream AMV leader sequence for the enhanced transcriptional activity obtained thereby. In addition, if the inserted coding region in itself codes for a truncated protein product, instead of deleting just the *B.t.* coding region from pAMVBTS between the Nco I site and the Pst I site, the deletion can be from the Nco I site to the Bcl I site, which is before the proline codons and the terminator codons, so that those can be retained with the expression plasmid for the new sequence. In any event, it should be clear that these plasmids are suitable for the insertion and expression of other coding sequences besides that illustrated herein.

EXAMPLE 2

Transformation and Regeneration of Transgenic Tobacco Plants

The plasmid pTV4AMVBTS was conjugated into *A. tumefaciens* strain EHA101 in a manner similar to that described in Barton et al. "Regeneration of Intact Tobacco Plants Containing Full Length Copies of Genetically Engineered T-DNA, and Transmission of T-DNA to R-1 Progeny," *Cell*, 32, p. 1033–1043 (1983). Seeds of tobacco (*Nicotiana tabacum*, var. Havana 425) were surface sterilized, and germinated on Murashige and Skoog (MS) medium. Aseptically grown immature stems and leaves were then inoculated with overnight cultures of *A. tumefaciens* harboring the plasmid pTV4AMVBTS. Following 48 to 72 hours of incubation at room temperatures on a regeneration medium (MS medium containing 1 milligram per milliliter of kinetin), cefotaxime (at 100 micrograms per milliliter) and vancomycin (at 250 micrograms per milliliter) were applied to kill the agrobacteria, and kanamycin (at 100 micrograms per milliliter) was applied to select for transformant plant tissue. After approximately 6 weeks, with media changes performed at 2 week intervals, shoots appeared. The shoots were excised and placed in rooting medium containing 25 milligrams per milliliter kanamycin until roots were formed, which occurred in 1 to 3 weeks. After roots were formed, the plants were transferred to commercial potting soil mixture (Metro-mix 360, W. R. Grace & Co.). Approximately 2 weeks after potting, insect toxicity tests were initiated on leaves of the resulting plants.

Insect Toxicity Assays

Insect eggs of tobacco hornworm (*Manduca sexta*), tobacco budworm (*Heliothis virescens*), corn earworm or cotton bollworm (*Heliothis zea*) and beet armyworm (*Spodoptera frugiperda*) were hatched on mature wild-type tobacco plants. Larvae of the various insects were allowed to graze for 1 to 3 days on wild-type plants prior to transfer to test plants. Since mature tobacco plants contained higher levels of secondary metabolites than freshly regenerated plants, the feeding of the larvae on older plants made the larvae less sensitive to toxins than neonatal larvae. This reduced sensitivity in the larvae proved useful in distinguishing between variations in the level of toxin production in various transgenic plants. Tobacco hornworms were placed directly on the leaves of young wild-type and recombinant plants, usually 2 to 4 larvae per plant per test, with up to 6 successive tests conducted per plant. Only test plants showing 100% toxicity to the larvae in all tests were considered to be resistant. Alternatively, tests were conducted using excised leaf tissue in petri dishes with 5 to 10 hornworms or a single larvae of the other species per dish. In the assays conducted in dishes, weights of the larvae were recorded at initiation and termination of the tests. Feeding trials were generally conducted for 2 to 4 days in duration, with daily monitoring of the reduction in feeding and larval deaths.

Table I below illustrates the toxicity of ten resulting transgenic plants as measured by these insect assays. Relative levels of toxicity between plants providing complete larvae mortality are subjective (indicated by scale of +to ++++), and are based on the extent of damage to the plant before mortality. In all cases of mortality, some feeding was observed. In Table 1, the number of gene inserts is listed as measured by restriction mapping and the level of toxin-related RNA was measured and is valued in picograms per 20 microgram in each plant. The toxicity ratio is number of larvae killed versus number tested. H425 is the wild-type (control) plant. "nd" indicated not detectable.

TABLE I

TOXICITY IN REGENERATED AMVBTS TOBACCO PLANTS

| PLANT # | GENES | RNA | TOXICITY |
|---|---|---|---|
| H425 | 0 | nd | − (0/50) |
| 857 | 3 | 47 | ++++ (12/12) |
| 858 | nd | 1.2 | − (1/6) |
| 859 | 2 | 1.1 | +++ (10/10) |
| 860 | 1 | 0.8 | +++ (8/8) |
| 861 | 2 | 1.4 | ++ (8/8) |
| 862 | 5 | 7 | ++++ (8/8) |
| 863 | 1 | 0.5 | + (6/6) |
| 870 | 3 | 2.5 | +++ (10/10) |
| 872 | 3 | 1.3 | ++ (8/8) |
| 884 | nd | 2.8 | − (2/6) |

Further analysis of over 100 independent transformations has shown that within approximately 25% of the plants feeding on the leaves by larvae is lethal to all larvae within 4 days, with the most resistant plants allowing only minimal feeding during the early hours of the test. Many of the plants which were judged nontoxic by the methods described for Table I resulted in few larvae being killed but did reduce larval feeding levels and growth rates in comparison to control tissues.

Blot Analysis

Southern Blot analyses were conducted on 10 of the regenerated transgenic plants of Table I above. Digestion of the DNA from the plants with Pst I and Xho I fragments would be expected to release from the transgenic plants the toxin chimera as a 2.42 kilobase internal DNA fragment which includes both the CaMV promoter and the entire toxin coding region from pTV4AMVBTSH. Eight of the 10 plants analyzed by Southern Blot appeared to have one or more intact toxin genes while two of the plants showed only broken inserts of variable size less than a single copy in intensity. Additional digests to analyze the border fragments of the recombinant plant DNA indicated that each of the transformants with intact genes contained between 1 and 3 different inserts, each of which hybridized at a single-copy intensity. The relative proportion of intact inserts, copy numbers, and the overall frequency of regeneration in these and other transgenic plants compares favorably with the experience with other genes in plants and supports the concept that the truncated B.t. toxin encoded by pAMVBTS and its progeny does not have the deleterious effects on plant cells that are observed when the full length protoxin coding region is inserted into plant cells.

Northern Slot-Blot analysis was conducted on 10 transformants. As may be seen in Table 1, the range of expression in horn worm-resistance transformants varied over a 50-fold range. The two plants which showed only broken inserts still showed evidence of toxin related mRNAs.

Immunoblot analysis of toxin-related polypeptides in the plants was also conducted. Specific immunoreactive polypeptides were discovered of approximately 72 kilodaltons. Control plant tissues did not contain the 72 kilodalton polypeptide.

Transmissibility of Transgenic Genes

Transmission of the resistance to insect predation to the progeny of transgenic plants was tested by allowing transgenic plants to flower, and then recovering the seed generated by self-pollination of the transgenic plants. The progeny of 1 plant, number 857 identified in Table I above, having a particularly high level of RNA activity, were analyzed in detail. It was determined that plant number 857 had 3 independent insertions of this chimeric sequence containing the toxin gene. Among the progeny, restriction mapping including border digests revealed that various combinations of the 3 inserts were found in the progeny from plant number 857. The levels of toxin related RNA activity in the progeny also appeared to vary. It was ascertained that the three inserts did not express at identical levels, since only marginal toxicity and little toxin-related RNA activity was apparent when the toxin insert characterized by the 1.5 kilobase border fragment was the only insert present. Table II summarizes the data on insect bioassays and nucleic acid analysis for the progeny of plant number 857. In Table 2, the inserts are labelled "a", "b", and "c". Additional analyses of progeny from other transgenic have indicated that the AMVBTS gene routinely continues to express in the progeny, at a level depending on the copy number and activity of the particular insertion.

TABLE II

TOXICITY IN PROGENY OF AMVBTS PLANT #857

| PLANT # | GENES | RNA | TOXICITY |
|---|---|---|---|
| H425 | 0 | nd | − (0/26) |
| 1262 | c | nd | − (3/6) |
| 1263 | c | nd | − (0/6) |
| 1264 | nd | nd | − (0/6) |
| 1265 | a, b, c | 6 | +++ (6/6) |
| 1266 | a, b, c | 6 | +++ (6/6) |
| 1267 | a, b, c | 5 | +++ (6/6) |
| 1268 | a, b, c | 12 | +++ (6/6) |
| 1269 | c | nd | − (2/6) |
| 1270 | c | nd | − (4/6) |
| 1271 | c | nd | − (0/6) |

TABLE II-continued

TOXICITY IN PROGENY OF AMVBTS PLANT #857

| PLANT # | GENES | RNA | TOXICITY |
|---------|-------|-----|----------|
| 1272 | a, b, c | 8 | ++++ (6/6) |
| 1273 | c | nd | − (2/6) |
| 1274 | a, b, c | 24 | ++++ (6/6) |
| 1275 | c | nd | − (4/6) |
| 1276 | a, b, c | 15 | ++++ (6/6) |

Verification of Toxicity

While the tobacco hornworm larvae were used as convenient assays for toxicity, because of the sensitivity of tobacco hornworms to B.t. toxin, the effect of the toxin on other Lepidopteran insects was also verified. The resistance of the toxin producing plants to predation by cotton bollworms, corn earworms, and beet armyworms was also tested. In successive tests using either the parent plant 857, or its progeny with all three insertions represented (for example plant number 1265), reductions in feeding and increased mortality of each species of larvae were observed relative to larvae fed on control non-transgenic tobacco tissues.

EXAMPLE III

Transgenic Cotton

It has been previously demonstrated generally that plant transformation vectors and techniques suitable for the Agrobacterium-mediated transformation of tobacco plants can be utilized in tissues of cotton (*Gossypium hirsutum L.*) plants. A description of the technique for doing this transformation, and the subsequent regeneration process necessary to recover full plants has been published. Umbeck et al., "Genetically Transformed Cotton (*Gossypium hirsutum L.*) Plants," *Bio/Technology*, 5, pp. 263–266 (1987). Since Lepidopteran insects are significant predators to cultivated cotton, the creation of transgenic cotton plants expressing the *B.t.* toxin specific to Lepidopteran pests was an appropriate objective.

Seeds of cultivated cotton of variety Coker 312, were surface sterilized with 3% sodium hypochlorite for 20 minutes. The seeds were then rinsed three times with sterile distilled water plus cefotaxime (500 mg/l). The seeds were then allowed to germinate on Stewart and Hsu (SH) medium containing the fungicide benomyl (50 mg/l). Four to six days after germination, hypocotyl explants were removed, cut into 0.5 cm pieces and placed on a support medium containing agar (0.8%) and water.

The hypocotyl pieces in culture were then inoculated with the diluted (1:10) overnight culture of a nontumorigenic or "helper" *A. tumefaciens* strain EHA101 harboring the vector pTV4AMVBTSH. The suspension culture of *A. tumefaciens* contained approximately $10^8$ bacteria per milliliter.

As in the previous experiment, the *A. tumefaciens* strain harbored a binary Ti plasmid system containing a Ti plasmid carrying the so-called virulence region and also the plasmid pTV4AMVBTSH. The infection by *A. tumefaciens* on the immature tissues was allowed to proceed for 3 days of incubation at room temperature. Cultures were maintained under normal room light conditions during incubations. After infection, the tissues were transferred to MS salts with B5 vitamins plus antibiotics, the phytohormones 2,4-D (0.1 mg/l) and either 6-furfurylaminopurine (0.1 mg/l) or zeatin (0.001 mg/l), and the gelling agent Gelrite (1.6 g/l), plus magnesium chloride (750 mg/l), plus 30 g/ glucose. Antibiotics were then added to the medium to kill the remaining Agrobacterium including cefotaxime (50–100 mg/l) and carbenicillin (400–500 mg/l). Kanamycin sulfate (5–50 mg/l) was also included in the medium as a selection agent for transformed tissues. Subcultures of the tissues were made every 3 to 6 weeks to replenish depleted nutrients and antibiotics. After 3 to 4 months, individually derived cell lines were labeled and maintained on the selection medium for tissue amplification. The tissues were incubated at 30 degrees C. for a 16 hour photoperiod (50–100 umol/$m^2$/S).

After amplification, the antibiotics were discontinued and the transformed tissues were maintained on the same mediums without plant hormones.

Embryogenic calli and embryos were obtained from the transformed and selected tissues using the method described in Umbeck et al., *supra*. When sufficient callus tissue was generated, Southern Blot analysis of the tissues was conducted in a manner identical to that conducted with the tobacco tissues detailed earlier. Embryogenic calli which were assayed showed the presence of one or more copies of the insert from pAMVBTS. In accordance with the published procedure, embryos which reached a selected size, i.e. about 4 mm or more in length, and which appeared to have good embryo development, with cotyledon and radicle present, were transferred to a rooting medium. This was done by soaking the embryos in a rooting medium (MS salts, glucose, and B5 vitamins) until root germination after which the seedlings were transferred to SH medium in an agar formulation until new leaves were formed. The rooting SH medium sometimes included the phytohormone gibberellic acid, at 0.1 mg/l. The embryos were then incubated at 30 degrees C and a 16 hour photoperiod. The embryos germinated, and at the 2 to 3 leaf stage were transferred to pots filled with vermiculite or soil, and watered and fertilized as needed. The plants were enclosed in a beaker for hardening-off the leaves and then were transferred to the greenhouse. Adapted plants were repotted in a commercial soil mixture such as Metro-Mix 360 and maintained until mature.

The resultant transgenic cotton plants did constitutively expressed the truncated toxin portion of the *B.t.* delta-endotoxin crystal protein. Suitable insect toxicity assays performed in the same fashion as indicated above with respect to the tobacco tissues confirmed the presence of and expression of the chimeric *B.t.* gene construction transferred from pTV4AMVBTSH into the genome of the cotton plants.

Leaf tissue from transgenic cotton plants transformed with the AMVBTS gene segment were fed to corn earworms (*Heliothis zea*). Corn earworm eggs were hatched and after 3 or 4 days of feeding on control cotton leaf tissue, were transferred to leaf tissue obtained from the transgenic cotton plants. Twelve worms were used for each treatment and were maintained in individual containers. Pesticide-free leaf material was replenished from the plants as needed. The trials were run until all the worms had died or pupated. Southern blots were also conducted to verify or negate gene presence. The results are summarized in the following Table III.

TABLE III

| Plant No. | Result of Southern | Number of Escapes | Number Dead After Feeding | Pupation Rate | Death Rate |
|---|---|---|---|---|---|
| Control | − | 4 | 4 | 50 | 50 |
| 3004 | + | 2 | 8 | 20 | 80 |
| 3005 | + | 0 | 11 | 8.5 | 92 |
| 3006 | + | 4 | 7 | 12.5 | 88 |
| 3012 | + | 0 | 12 | 0 | 100 |
| 3018 | − | 6 | 3 | 50 | 50 |

Plant 3018 was a transgenic cotton plant that carried the T-DNA construction with an inactive *B.t.* gene.

The mean weight of the living worms was measured after 15 days of feeding in the following Table IV.

TABLE IV

| Plant No. | No. Worms Feeding | Mean Fresh Weight (g) |
|---|---|---|
| Control | 8 | 0.1215 |
| 3004 | 5 | 0.1520 |
| 3005 | 7 | 0.0853 |
| 3006 | 3 | 0.0320 |
| 3012 | 8 | 0.0536 |
| 3018 | 4 | 0.1064 |

Further insect feeding tests were also conducted with cabbage looper (*Trichoplusia ni*) and also demonstrated an adverse effect on the worms although again the effect varied somewhat from plant to plant. These results indicate that Agrobacterium-mediated transformation of cotton is similar to that previously reported for tobacco. Agrobacterium-mediated transformation of tobacco, as recited in Example 2 above, results in transmission of the transgenic genes to the progeny through seed.

In order to enable others of ordinary skill in the art to practice the present invention, certain deposits have been made, all hosted in *E.coli*, with the American Type Culture Collection, 12301 Park Lawn Drive, Rockville, Md. U.S.A. on the dates listed below and with the following ATCC accession numbers. Similar deposits have also been made with the Cetus Master Culture Collection maintained by Cetus Corporation, Emeryville, Calif., and the CMCC Accession number of these cultures is also given below.

| PLASMID | CMCC # | ATCC # | ATCC DEPOSIT DATE |
|---|---|---|---|
| pCMC92 | 2306 | 53093 | April 10, 1985 |
| pCMC122 | 1991 | 39639 | March 23, 1984 |
| pCMC1022 | 2902 | 67269 | November 14, 1986 |
| pAMVBTS | 3137 | 53637 | June 24, 1987 |
| pTV4AMVBTSH | 3136 | 53636 | June 24, 1987 |

The present invention is not to be limited in scope by the microorganisms or plasmids deposited herein, since the deposited embodiment is intended as a single illustration of one aspect of the invention and to enable a single illustration of practice of the invention, and any microorganisms or plasmids which are functionally equivalent are within the scope of this invention. Indeed, various modifications of the invention in addition to those shown and described herein will become apparent to those skilled in the art from the foregoing description and fall within the scope of the appended claims.

What is claimed is:

1. A dicot plant comprising in its genome a copy of a gene construction consisting essentially of, in sequence 5' to 3':
   a promoter sequence effective to initiate transcription in plant cells;
   a translational enhancer sequence from the transcribed but untranslated sequence immediately preceding the coding region of an alfalfa mosaic virus coat protein gene;
   a protein coding sequence for a protein of less than about 700 amino acids, the protein being a *Bacillus thuringiensis* delta-endotoxin which is toxic upon ingestion to *Manduca sexta*; and
   a polyadenylation sequence, the gene construction effectively expressing in the plant cells a protein toxic to *Manduca sexta*;
   wherein the plant is cotton.

2. Seed of the plant of claim 1.

3. A dicot plant comprising plant cells which are toxic to *Manduca sexta* upon ingestion, the plant cells comprising in their genome an expressed protein coding sequence consisting essentially of a DNA sequence coding for a *Bacillus thuringiensis* delta-endotoxin protein of less than about 700 amino acids which imbues the cells with lethal toxicity to *Manduca sexta*, the protein coding sequence immediately preceded by a translational enhancer sequence from the untranslated leader sequence of an alfalfa mosaic virus coat protein, wherein the plant is cotton.

4. Seed of the plant of claim 3.

5. A cotton plant comprising cells which are lethally toxic upon ingestion to *Heliothis zea*, the cotton cells comprising in their genome an expressed protein coding sequence consisting essentially of a DNA sequence coding for a protein of less than about 700 amino acids which is an amino-terminal portion of a *Bacillus thuringiensis* delta endotoxin which imbues the cells with lethal toxicity to *Heliothis zea*.

6. A cotton plant comprising cells which are lethally toxic upon ingestion by *Heliothis zea*, the cotton cells comprising in their genome an expressed protein coding sequence consisting essentially of a DNA sequence coding for a protein of the amino acid sequence set forth in FIG. 5.

7. Seed of the plant of claim 5.

* * * * *